(12) United States Patent
Youn et al.

(10) Patent No.: US 9,144,593 B2
(45) Date of Patent: Sep. 29, 2015

(54) PHARMACEUTICAL COMPOSITION FOR PREVENTING OR TREATING TH17-MEDIATED DISEASE COMPRISING POLY-GAMMA-GLUTAMIC ACID

(71) Applicant: Industry-University Cooperation Foundation Hanyang University, Seongdong-gu, Seoul (KR)

(72) Inventors: Jeehee Youn, Seoul (KR); Kyuheon Lee, Seoul (KR); Sejin Hwang, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 0 days.

(21) Appl. No.: 13/678,225

(22) Filed: Nov. 15, 2012

(65) Prior Publication Data

US 2013/0267463 A1    Oct. 10, 2013

(30) Foreign Application Priority Data

Apr. 10, 2012  (KR) .................. 10-2012-0037414

(51) Int. Cl.
| | |
|---|---|
| A61K 38/00 | (2006.01) |
| A61P 19/02 | (2006.01) |
| A61P 29/00 | (2006.01) |
| C07K 14/47 | (2006.01) |
| C07K 17/00 | (2006.01) |
| C07K 16/00 | (2006.01) |
| C07K 5/00 | (2006.01) |
| C07K 7/00 | (2006.01) |
| A61K 38/02 | (2006.01) |
| C07K 5/02 | (2006.01) |
| C07K 2/00 | (2006.01) |

(52) U.S. Cl.
CPC ............... *A61K 38/02* (2013.01); *A61K 38/00* (2013.01); *C07K 2/00* (2013.01); *C07K 5/02* (2013.01); *C07K 5/0215* (2013.01)

(58) Field of Classification Search
None
See application file for complete search history.

(56) References Cited

U.S. PATENT DOCUMENTS

| | | | | |
|---|---|---|---|---|
| 7,364,875 | B2 * | 4/2008 | Prescott et al. | 435/68.1 |
| 2004/0043030 | A1 * | 3/2004 | Griffiths et al. | 424/178.1 |
| 2012/0196806 | A1 * | 8/2012 | Sung et al. | 514/14.9 |

OTHER PUBLICATIONS

Kim et al., "*Bacillus subtilis*-specific poly-gamma-glutamic acid regulates development pathways of naive CD4 positive T cells through antigen-presenting cell-dependent and -independent mechanisms," Intl. Immunol. 21:977-990 (2009).*

Lee et al., "*Bacillus*-derived poly-gamma-glutamic acid reciprocally regulates the differentiation of T helper 17 and regulatory T cells and attenuates experimental autoimmune encephalomyelitis," Clin. Exper. Immunol. 170:66-76 (first available online Sep. 3, 2012).*

Lee, K. et al. "Microbe-associated Molecular Pattern Poly-γ-glutamic Acid Reciprocally Regulates the Differentiation of Th17 and Regulatory T cells and Suppresses Experimental Autoimmune Encephalomyelitis." The 2011 Fall Conference of the Korean Association of Immunologists, Nov. 17-18, 2011.*

Aranami et al., "Th17 Cells and Autoimmune Encephalomyelitis (EAE/MS)," Allergology Intl. 57:115-120 (2008).*

Kim et al., "*Bacillus subtilis*-specific poly-gamma-glutamic acid regulates development pathways of naive CD4+ T cells through antigen-presenting cell-dependent and -independent mechanisms," Intl. Immunol. 21:977-990 (2009).*

Simpson, et al., "Mindfulness based interventions in multiple sclerosis—a systematic review," BMC Neurology 14:15 (2014).*

Sung, et al., "Natural and Edible Biopolymer Poly-gamma-glutamic acid: Synthesis, Production, and Applications," The Chemical Record 5:352-366 (2005).*

\* cited by examiner

*Primary Examiner* — James H Alstrum Acevedo
*Assistant Examiner* — Thea D' Ambrosio
(74) *Attorney, Agent, or Firm* — Harness, Dickey & Pierce

(57) ABSTRACT

Provided are a pharmaceutical use of poly-gamma-glutamic acid used for preventing or treating Th17-mediated diseases, a composition for preventing or treating Th17-mediated diseases comprising poly-gamma-glutamic acid as an active ingredient, and a method of preventing or treating Th17-mediated diseases using the same. The pharmaceutical composition is effective in inhibiting the differentiation of Th17 cells while promoting Treg cells, and, thus, can be useful in preventing or treating Th17-mediated diseases such as multiple sclerosis, rheumatoid arthritis, systemic lupus erythematosus, inflammatory bowel disease, Crohn's disease, ankylosing spondylitis, and the like.

5 Claims, 14 Drawing Sheets

(a) Normal control (b) MOG (c) MOG/γPGA

PHARMACEUTICAL COMPOSITION FOR PREVENTING OR TREATING TH17-MEDIATED DISEASE COMPRISING POLY-GAMMA-GLUTAMIC ACID

CROSS-REFERENCES TO RELATED APPLICATION

This patent application claims the benefit of priority from Korean Patent Application No. 2012-0037414, filed on Apr. 10, 2012 in the Korean Intellectual Property Office (KIPO), the entire contents of which are incorporated herein by reference.

BACKGROUND OF THE INVENTION

1. Field of the Invention

Example embodiments of the present invention relate in general to the field of a pharmaceutical use of poly-gamma-glutamic acid used for preventing or treating Th17-mediated diseases, and more specifically, to a pharmaceutical composition for preventing or treating Th17-mediated diseases including poly-gamma-glutamic acid as an active ingredient.

2. Description of the Related Art

A human body in general raises a defensive immune response against foreign substances, but is not reactive against substances in his or her own body. The above phenomenon in which the human body is not immune against substances in his or her own body is known as 'immunological self-tolerance.' In order to maintain this phenomenon, the body operates two different mechanisms: (1) a 'clonal deletion' mechanism by central immune organs to eliminate T cells which are reactive to autoantigens and (2) a 'regulation' mechanism by peripheral immune organs to suppress the activities of T cells which are reactive to autoantigens. Failure of the immunological self-tolerance causes autoimmune diseases.

Regulatory T (Treg) cells are major suppressor cells that mediate the above 'regulation' mechanism. The Treg cells were originally known as a minor population of cells generated in the thymus via an intrinsic pathway and distributed in the periphery, but they are now known to be generated in the periphery as well. That is, naïve CD4+ T cells, which are present in the periphery rather than the thymus, can express Foxp3 in response to antigenic stimulation in the presence of TGF-β, and differentiate into Treg cells. These Treg cells play a crucial role in the mechanism of 'immunological self-tolerance.'

In contrast, Th17 cells are representative proinflammatory cells. Th17 cells, being a different subset from Th1 and Th2 cells, secrete IL-17, IL-17F, IL-21, and IL-22. Naïve CD4+ T cells can be differentiated into Th17 cells in vitro in response to antigenic stimulation in the presence of TGF-β and IL-6, and transcription factors such as RORγt, STAT-3, and IRF4 are involved in this process. Th17 cells infiltrated into the peripheral tissues act on macrophages, dendritic cells, fibroblasts, vascular endothelial cells, osteoclasts, etc., and secrete various inflammatory cytokines (IL-1, TNF, IL-8, IL-6, etc.), chemokines, MMPs, etc., thereby causing tissue damage. These Th17 cells are major pathologic cells that mediate inflammatory diseases.

As described above, Treg cells and Th17 cells are contrary to each other in their roles, but their generations in the periphery share the common precursor cells and are interrelated. That is, when CD4 positive T cells are differentiated by TGF-β and antigenic stimulation, whether they are differentiated into Treg cells or Th17 cells is determined based on the presence of other inflammatory cytokines such as IL-6, IL-23, IL-1, and IL-21. Therefore, in Th17-mediated diseases which are caused by the imbalance in Th17/Treg or the over-differentiation of Th17 cells, any substance which can suppress the generation of Th17 cells while inducing the generation of Treg cells may be able to remedy the above imbalance and restore immune-homeostasis, thereby being useful for preventing and treating such diseases.

Recently, intensive research has been conducted for the development of a therapeutic agent which can suppress the generation of Th17 cells. As a result, various therapeutic agents, for example, SR1001, which inhibits RORγt, a transcription factor of Th17 cells, Halofuginone, which inhibits only Th17 activity, and anti-IL-17 monoclonal antibody, etc., have been developed. However, these substances have disadvantages in that a great deal of time will be required before they become applicable to patients after undergoing clinical trials, and also in the case of antibodies, the cost to prepare monoclonal antibodies may be prohibitively expensive. Therefore, there is an urgent need for the development of a novel therapeutic agent which is reasonable in cost and is easily applicable to humans while having an excellent therapeutic effect in preventing or treating Th17-mediated diseases.

SUMMARY OF THE INVENTION

Accordingly, example embodiments of the present invention are provided to substantially obviate one or more problems due to limitations and disadvantages of the related art.

Example embodiments of the present invention provide a pharmaceutical composition which is effective in preventing or treating Th17-mediated diseases, reasonable in cost, and applicable to humans without any adverse side effects.

Example embodiments of the present invention also provide a composition for preventing or treating Th17-mediated diseases comprising poly-gamma-glutamic acid as an active ingredient.

In some example embodiments, there is provided a method of preventing or treating Th17-mediated diseases comprising administering a pharmaceutically effective amount of poly-gamma-glutamic acid to a subject with Th17-mediated diseases or one who is vulnerable to the disease.

BRIEF DESCRIPTION OF THE DRAWINGS

Example embodiments of the present invention will become more apparent by describing in detail example embodiments of the present invention with reference to the accompanying drawings, in which.

DESCRIPTION OF THE PREFERRED EMBODIMENTS

Figure 1:
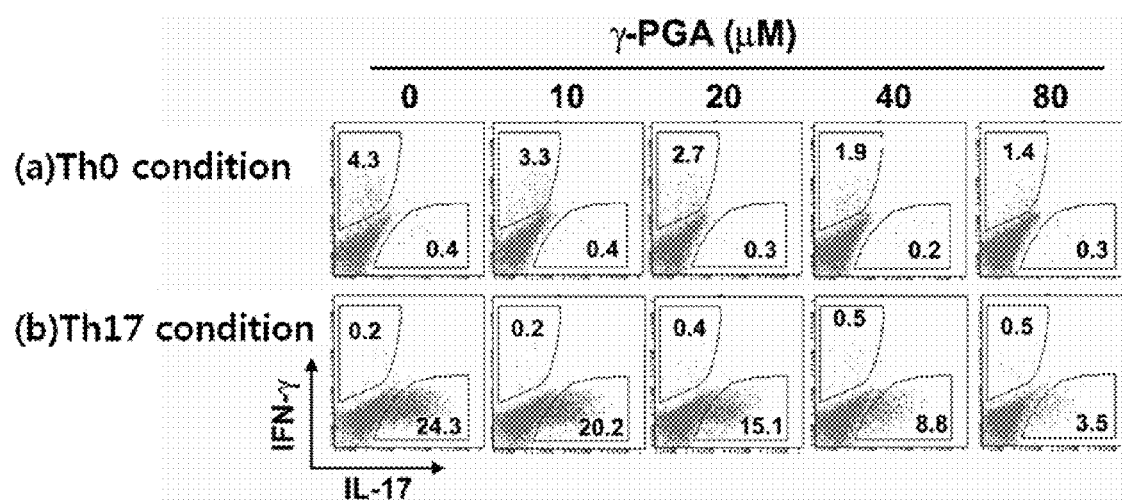
FIG. 1 is a graph illustrating the effect of poly-gamma-glutamic acid on the differentiation of naïve CD4+ T cells into Th17 cells under Th0 differentiation conditions (a) and Th17 differentiation conditions (b) via flow cytometric analysis using an anti-IL-17-PE antibody and an anti-IFN-γ-FITC antibody.

Example embodiments of the present invention are disclosed herein. However, specific structural and functional details disclosed herein are merely representative for purposes of describing example embodiments of the present invention, however, example embodiments of the present invention may be embodied in many alternate forms and should not be construed as limited to example embodiments of the present invention set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures. It will be understood that, although the terms first, second, etc., may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising,"

"includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should also be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

The present invention is described herein below.

In an exemplary embodiment, the present invention provides a pharmaceutical composition for preventing or treating Th17-mediated diseases including poly-gamma-glutamic acid as an active ingredient.

In another exemplary embodiment, the pharmaceutical composition of the present invention includes poly-gamma-glutamic acid.

The poly-gamma-glutamic acid is a polymer in which glutamic acid is connected via a γ-amide bond. The poly-gamma-glutamic acid is produced during fermentation of beans by *Bacillus subtilis*, and it is a natural compound accounting for about 80% of viscous components of fermented soybean products such as cheonggukjang and nattō. The molecular weight of thus produced poly-gamma-glutamic acid may differ depending on the stains and the conditions for fermentation. In the present invention, the molecular weight of poly-gamma-glutamic acid as an active ingredient of a pharmaceutical composition is preferably from about 1 kDa to 2000 kDa, but the present invention is not limited thereto. In an Example Embodiment of the present invention, the poly-gamma-glutamic acid having a molecular weight of 50 kDa on average is used.

The poly-gamma-glutamic acid reduces or suppresses the differentiation of naïve T cells into Th17 cells. The poly-gamma-glutamic acid acts on naïve T cells and suppresses the expression of RORγt, a transcription factor which is essential for the differentiation of naïve T cells into Th17 cells, thereby preventing the differentiation of the naïve T cells into Th17 cells. More specifically, the poly-gamma-glutamic acid suppresses the expression of RORγt even when the naïve T cells are under a Th17 cell differentiation conditions. In an Example Embodiment of the present invention, CD4 positive T cells, one type of the naïve T cells, were cultured by exposing them to a Th17 differentiation conditions to induce their differentiation into Th17 cells, while concurrently treating them with poly-gamma-glutamic acid. As a result, the percentage of differentiation of CD4 positive T cells treated with poly-gamma-glutamic acid into Th17 cells, depending on the concentration of poly-gamma-glutamic acid, decreased up to ⅛, compared to that of CD4 positive T cells untreated with poly-gamma-glutamic acid (FIG. 1(b)). As such, the suppression of differentiation of the CD4 positive T cells into the Th17 cells appears to be due to the inhibition of the expression of RORγt, a transcription factor which is necessary for the differentiation of the naïve T cells into the Th17 cells by the treatment with poly-gamma-glutamic acid (FIG. 2(b)). Further, the suppression of the CD4 positive T cells into the Th17 cells also resulted in the decrease in the production of IL-17, a Th17 cell-specific cytokine (FIG. 3(b)). From the above-described results described in specific example embodiments, it was confirmed that the poly-gamma-glutamic acid is involved in a mechanism that suppresses the expression of RORγt thereby prohibiting the differentiation of naïve T cells into Th17 cells, and eventually inhibiting the production of IL-17.

Also, the poly-gamma-glutamic acid is known to increase or promote the differentiation of naïve T cells into regulatory T (Treg) cells. In particular, the poly-gamma-glutamic acid can promote the differentiation of the naïve T cells into the regulatory Treg cells not only when the naïve T cells are under a Th0 differentiation conditions but also when the cells are under a Th17 differentiation conditions. In a specific Example Embodiment of the present invention, CD4 positive T cells, one type of the naïve T cells, were cultured by exposing them to either a Th0 differentiation conditions or a Th17 differentiation conditions to induce their differentiation into Th17 cells, while concurrently treating them with poly-gamma-glutamic acid. The result revealed that there was an increase in the number of the CD4 positive T cells which expresses Foxp3 when treated with the poly-gamma-glutamic acid. More specifically, when the CD4 positive T cells (1) exposed under the Th0 differentiation conditions is treated with the poly-gamma-glutamic acid, the expression level of Foxp3 in the CD4 positive T cells increased up to about 5 times, depending on the concentration of the treated poly-gamma-glutamic acid (FIG. 2(a) and FIG. 5), and when the CD4 positive T cells (1) exposed under the Th17 differentiation conditions is treated with 40 μM of poly-gamma-glutamic acid, the expression level of Foxp3 in the CD4 positive T cells increased up to about 1.5 times (FIG. 2(b). From the results as described above, it was confirmed that poly-gamma-glutamic acid is effective in differentiating naïve T cells into Treg cells, and that this effect of poly-gamma-glutamic acid can be maintained even under the condition in which the naïve T cells are differentiated into Th17 cells.

That is, the poly-gamma-glutamic acid can effectively induce the differentiation of naïve T cells into Treg cells while suppressing the differentiation of naïve T cells into Th17 cells, even under the condition in which the naïve T cells are differentiated into Th17 cells. Therefore, the poly-gamma-glutamic acid can be used for the prevention or treatment of diseases caused by over-differentiation or over-growth of Th17 cells. When the Th17 cells are over-differentiated or over-grown, a relative decrease in the number of Treg cells results in an imbalance in immune system, thereby causing many Th17-mediated diseases due to the imbalance between the Th17 and Treg cells. That is, an environment which is formed in the immune system to promote the differentiation into the Th17 cells eventually becomes the cause of Th17-mediated diseases. In the above-mentioned Th17-mediated diseases, the poly-gamma-glutamic acid is effective to prevent or treat the Th17-mediated disease by regulating the imbalance between the Th17 cells and the Treg cells.

The Th17-mediated diseases are those caused by over-differentiation or over-growth of Th17 cells, and may include, but are not limited to, at least one selected from the group consisting of autoimmune diseases, inflammatory diseases, osteoclasia, and transplantation rejection of cells, tissue and organs. In particular, the above-mentioned Th17-mediated diseases may be one or more selected from the group consisting of Behçet's disease, polymyositis/dermatomyositis, autoimmune cytopenias, autoimmune myocarditis, primary liver cirrhosis, Goodpasture's syndrome, autoimmune meningitis, Sjögren's syndrome, systemic lupus erythematosus, Addison's disease, alopecia areata, ankylosing spondylitis, autoimmune hepatitis, autoimmune mumps, Crohn's disease, insulin-dependent diabetes mellitus, dystrophic epidermolysis bullosa, epididymitis, glomerulonephritis, Graves' disease, Guillain-Barré syndrome, Hashimoto's disease, hemolytic anemia, multiple sclerosis, myasthenia gravis, *pemphigus vulgaris*, psoriasis, rheumatic fever, rheumatoid arthritis, sarcoidosis, scleroma, spondyloarthropathy, thyroiditis, vasculitis, vitiligo, myxedema, pernicious anemia and ulcerative colitis.

In a specific Example Embodiment of the present invention, it was confirmed that multiple sclerosis and rheumatoid arthritis, representative of the above-mentioned Th17-mediated diseases, can be therapeutically treated by administration of the poly-gamma-glutamic acid.

Figure 9:
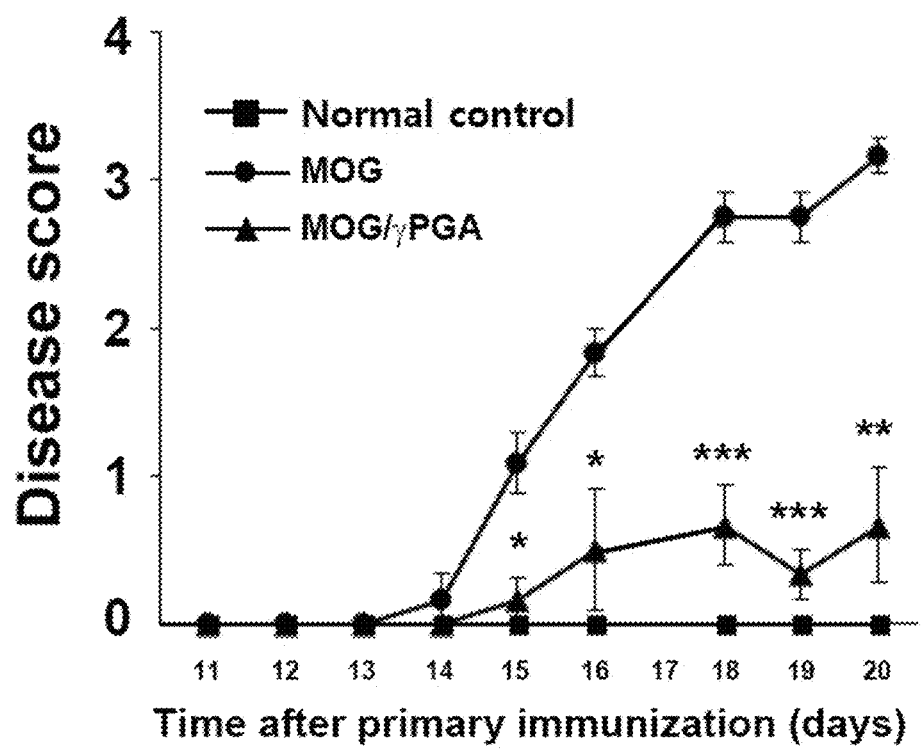
FIG. 9 is a graph illustrating the evaluation result of the effect of poly-gamma-glutamic acid on clinical symptoms in an EAE mouse model.
Figure 10:
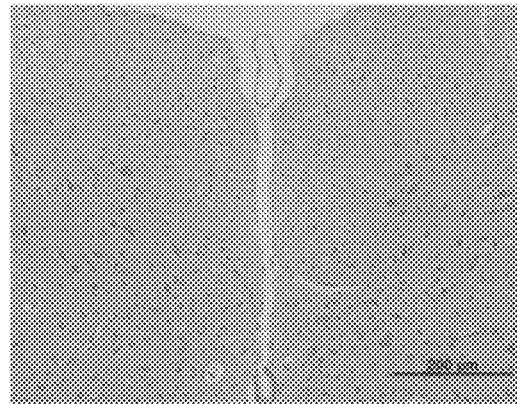
FIG. 10($a$) to FIG. 10($c$) are microscopic images showing the histopathological effect of poly-gamma-glutamic acid in an EAE mouse model.
Figure 10:
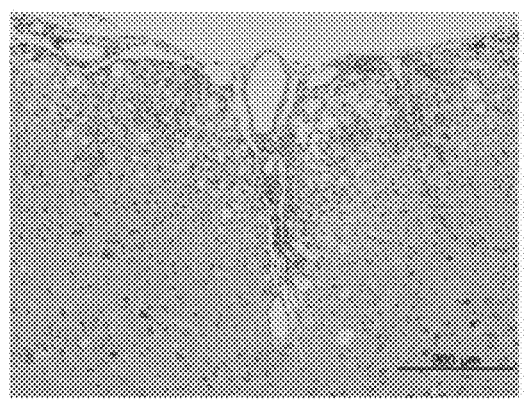
Figure 10:
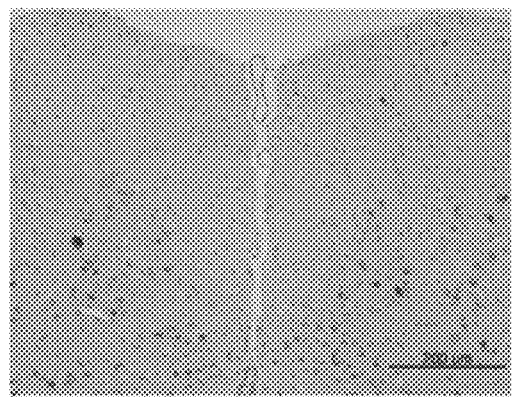

First, the therapeutic effect of the poly-gamma-glutamic acid was examined by administering poly-gamma-glutamic acid into a multiple sclerosis-induced mouse model. As a result, it was found that the number of inflammatory cells in the central nervous system of the mouse model was decreased by the administration of the poly-gamma-glutamic acid (FIG. 11 and FIGS. 12(*a*) and (*b*)), while the number of Treg cells in the immune system increased (FIGS. 12(*c*) and (*d*)). In addition, it was found that the clinical and histopathological symptoms of the mouse model were greatly alleviated (FIG. 9 and FIG. 10).

Figure 13:
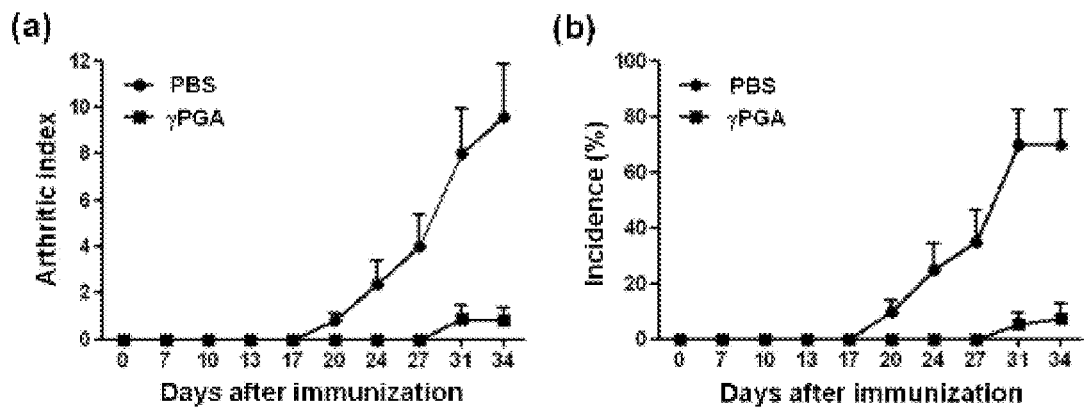
FIG. 13 shows graphs confirming the suppressive effect of poly-gamma-glutamic acid on severity (a) and incidence (b) of arthritis in a rheumatoid arthritis model.
Figure 14:
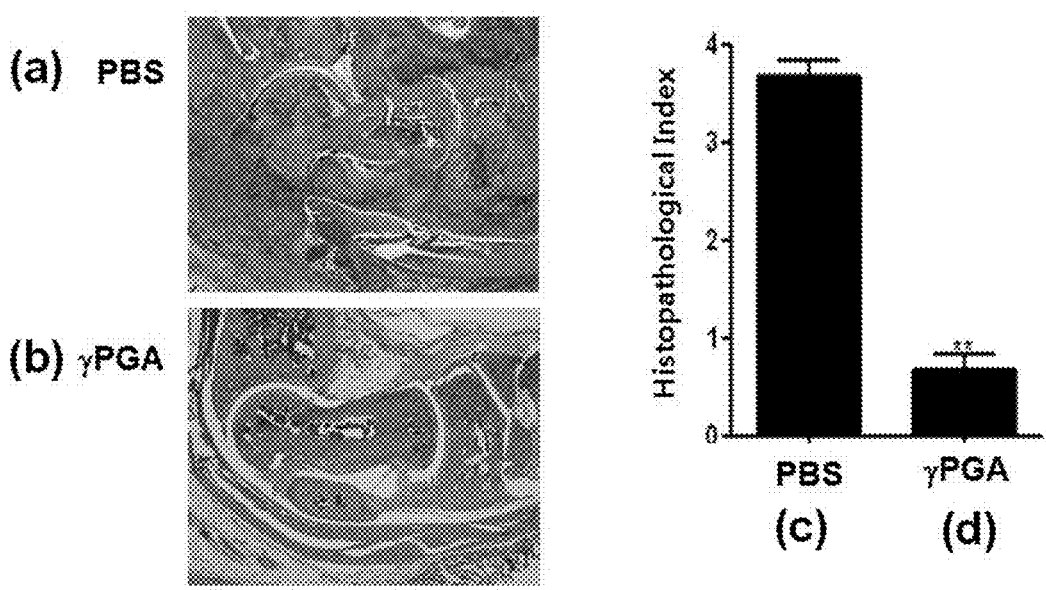
FIG. 14 shows microscopic images depicting the histopathological effect of poly-gamma-glutamic acid on the suppression of arthritis ((a) and (b)), and their scoring graphs ((c) and (d)) in a rheumatoid arthritis model.
Figure 15:
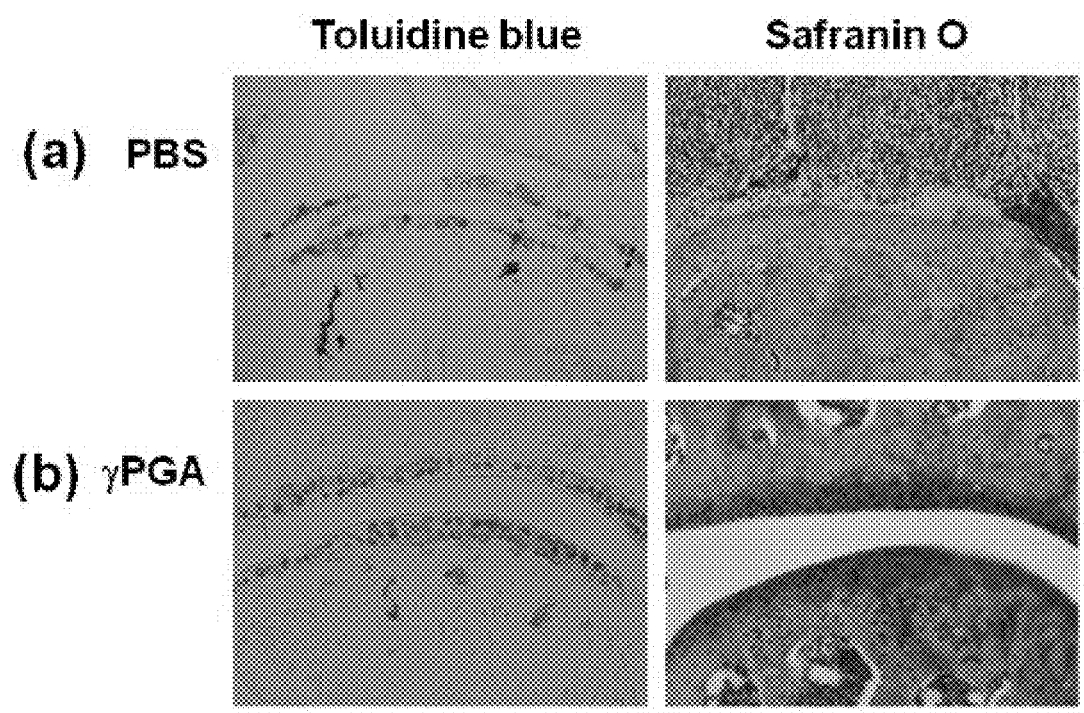
FIG. 15($a$) and FIG. 15($b$) are microscopic images showing the histopathological effect of poly-gamma-glutamic acid on the protection of joint cartilage in a rheumatoid arthritis model.
Figure 16:
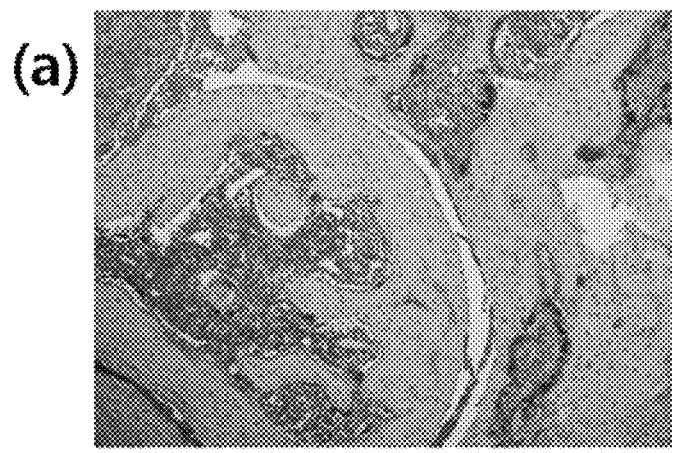
FIG. 16 shows microscopic images confirming the distribution of osteoclasts from a joint in a rheumatoid arthritis model after untreating (a) or treating with poly-gamma-glutamic acid (b), and a graph showing the result of measurement of the number of osteoclasts from a joint in a rheumatoid arthritis model after treating or untreating with poly-gamma-glutamic acid (c)
Figure 16:
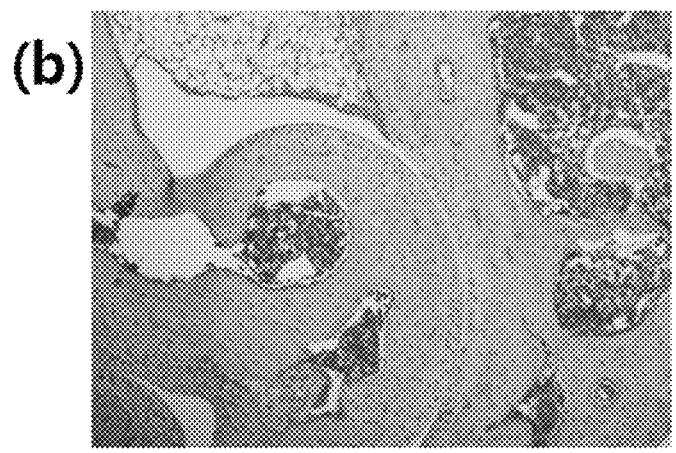
Figure 16:
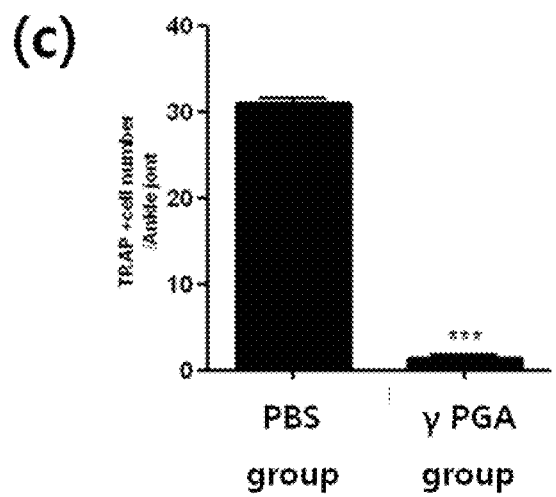
Figure 18:
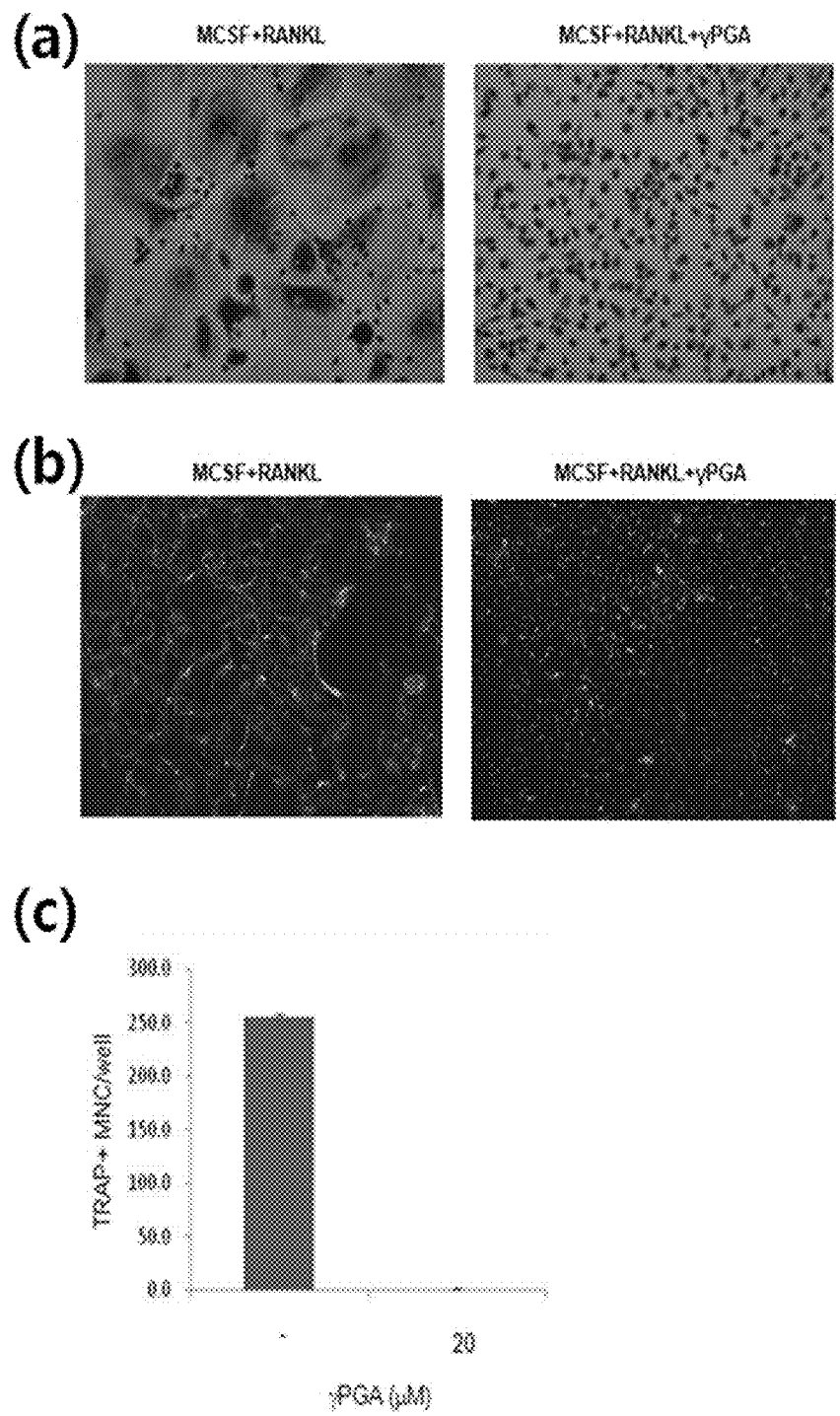
FIG. 18($a$) and FIG. 18($b$) are microscopic pictures depicting the result of a suppressive effect of poly-gamma-glutamic acid against the differentiation of human rheumatoid arthritis patient-derived osteoclast precursors into osteoclasts, thereby inhibiting actin ring formation, and FIG. 18($c$) is a graph depicting the number of osteoclasts after treating or untreating with poly-gamma-glutamic acid.
Figure 19:
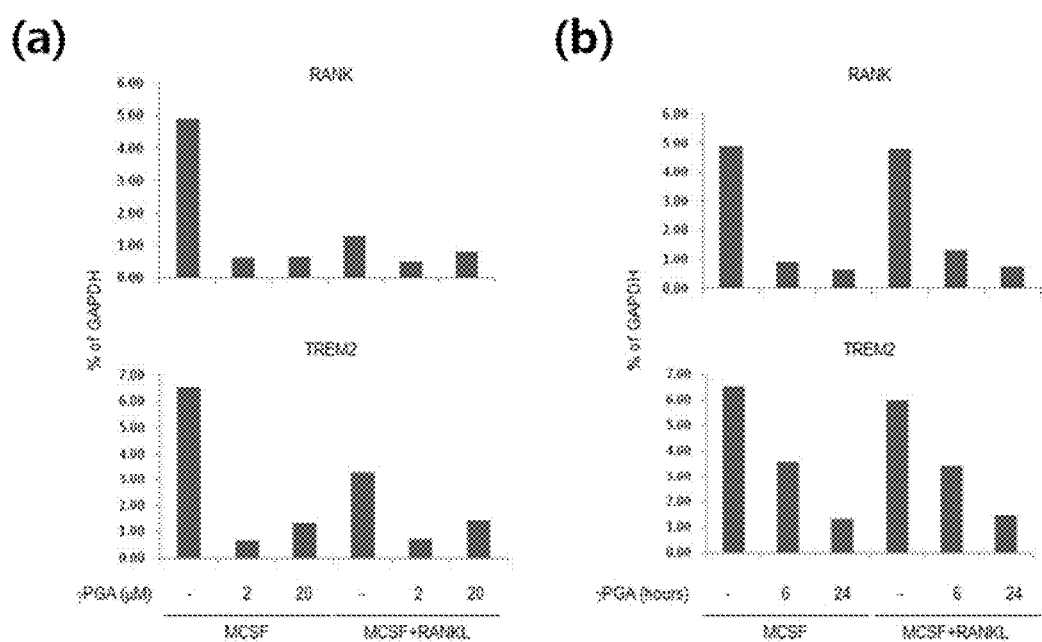
FIG. 19($a$) is a graph depicting the expression level of a RANK gene and a TREM2 gene according to the concentration of poly-gamma-glutamic acid after treating human rheumatoid arthritis patient-derived osteoclast precursors with poly-gamma-glutamic acid for 6 hours, and FIG. 19($b$) is a graph depicting the expression level of a RANK gene and a TREM2 gene according to the concentration of poly-gamma-glutamic acid after treating human rheumatoid arthritis patient-derived osteoclast precursors with 20 μM of poly-gamma-glutamic acid.

Further, the therapeutic effect of the poly-gamma-glutamic acid was examined by administering poly-gamma-glutamic acid into an animal model with rheumatoid arthritis, which is known to be a Th17 cell-dependent inflammatory disease and Th17 cell-dependent bone-destructive disease. As a result, it was found that the severity and incidence of arthritis were drastically reduced by the administration of poly-gamma-glutamic acid (FIG. 13), and the histopathological symptoms in joint tissues, talus and calcaneus were greatly improved (FIGS. 14 to 16). More specifically, the administration of the poly-gamma-glutamic acid resulted in (1) a drastic decrease in the number of inflammatory cells in the joint tissues (FIG. 14), and also (2) a drastic decrease in cartilage damage in joint tissues and the production of osteoclasts in the tali and calcanei (FIG. 15 and FIG. 16). Further, it was found that the administration of poly-gamma-glutamic acid suppressed the expression of RANK, i.e., a ligand of RANKL, the expression of which is increased by IL-17 secreted in Th17 cells, thereby inhibiting the differentiation of osteoclast precursors into osteoclasts and eventually reducing the production of osteoclasts (FIG. 18 and FIG. 19).

The pharmaceutical composition of the present invention preferably includes poly-gamma-glutamic acid as an active ingredient in the amount of 0.0001 to 50 wt %, but the present invention is not limited thereto. The pharmaceutical composition of the present invention may further include at least one pharmaceutically acceptable carrier for its administration in addition to the above active ingredient. A pharmaceutically acceptable carrier may be used in a mixture with at least one selected from a saline solution, sterile water, Ringer's solution, a buffered saline solution, a dextrose solution, a maltodextrin solution, glycerol, ethanol, liposome, and a mixture thereof, and upon necessity, other conventional additives such as an antioxidant, a buffer solution, a bacteriostat, etc., may be added. In addition, other additives such as a diluent, a dispersant, a surfactant, a binder or a lubricant may be further added to prepare the pharmaceutical composition in the form of an injectable formulation such as an aqueous solution, a suspension, and an emulsion; a pill; a capsule; granules; or a tablet. In order to make the pharmaceutical composition act specifically on target organs, target-specific antibodies or other ligands may be bound to the above carrier before use. Further, the pharmaceutical composition may be suitably formulated depending on the target diseases or components included therein using an appropriate method in the related art or methods disclosed in Remington's Pharmaceutical Science ($21^{st}$ edition), Mack Publishing Company, Easton, Pa.

The pharmaceutical composition may be administered inside or outside gastric organs according to its usage and application. The administration inside gastric organs includes oral administration, sublingual administration, rectal/vaginal administration, etc. The administration outside gastric organs includes intraperitoneal injection, blood stream injection, intramuscular and intravisceral injection, inhalation, administration into organs, and local administration into skin and mucosae.

The dose of the pharmaceutical composition varies depending on the body weight, age, sex, and health conditions of a patient, diet, administration time, method of administration, excretion rate, and severity of disease. The daily dose of the pharmaceutical composition is in the range of 0.00001 mg/ml to 100 mg/ml, and is preferably administered one to a few times daily.

Example embodiments of the present invention are disclosed herein. However, specific structural and functional details disclosed herein are merely representative for purposes of describing example embodiments of the present invention, and example embodiments of the present invention may be embodied in many alternate forms and should not be construed as limited to example embodiments of the present invention set forth herein.

Example 1

Induction of Differentiation into Th17/Treg Cells in the Presence of Poly-Gamma-Glutamic Acid <1-1> Preparation of CD4 Positive T Cells 6 to 8 week old male C57BL/6 mice were sacrificed in a specific pathogen-free barrier facility at Hanyang University, Korea, according to the regulations of Institutional Animal Care and Use Committee, and spleens and lymph nodes were obtained. The obtained spleens and lymph nodes were added into an RPMI1640 medium (hereinafter, 'RPMI/10F') supplemented with 10% fetal bovine serum (FBS), 100 unit/ml penicillin, 100 mg/ml streptomycin, 0.05 mM 2-mercaptoethanol and 2 mM L-glutamine, ground to extract cells, red blood cells and tissue residue were removed therefrom, and a single cell suspension was finally obtained. CD4 positive T cells were purified from the single cell suspension using a magnetic bead-activated cell sorting (MACS) method.

<1-2> Induction of Differentiation of CD4 Positive T Cells into Th17 Cells

Purified CD4 positive T cells obtained in Example <1-1> were aliquoted into a 5-well plate including 1 µg/ml anti-CD3 antibody (145-2C11; eBioscience, USA) and 1 µg/ml anti-CD28 antibody (37.51; BD Biosciences, USA), each at a concentration of $2 \times 10^6$ cells/well. Each of the above 5 wells was respectively treated with 50 kDa poly-gamma-glutamic acid (Bioleaders, Korea) at a concentration of 0, 10, 20, 40, and 80 µM, 20 ng/ml murine IL-6 (R&D Systems, USA), 5 ng/ml TGF-β (R&D Systems, USA), 5 µg/ml anti-IL-4 antibody (11b11; BD Biosciences, USA) and 5 µg/ml anti-IFN-γ antibody (XMG1.2; BD Biosciences, USA) (hereinafter, 'Th17 differentiation conditions') were respectively added thereto, and then culturing was performed in an RPMI/10F medium at a concentration of 1 ml/well in an incubator maintained at 37° C., 5% $CO_2$ for 4 days in order to induce the differentiation of CD4 positive T cells into Th17 cells.

<1-3> Induction of Differentiation of CD4 Positive T Cells into Treg Cells

Purified CD4 positive T cells obtained in Example <1-1> were aliquoted into a 5-well plate including 1 μg/ml anti-CD3 antibody (145-2C11; eBioscience, USA) and 1 μg/ml anti-CD28 antibody (37.51; BD Biosciences, USA), each at a concentration of $2\times10^6$ cells/well. Each of the above 5 wells was respectively treated with 50 kDa poly-gamma-glutamic acid (Bioleaders, Korea) at a concentration of 0, 10, 20, 40, and 80 μM, 4 ng/ml IL-2 (Peprotech, USA) was added thereto (hereinafter, 'Th0 differentiation conditions'), and then culturing was performed in an RPMI/10F medium at a concentration of 1 ml/well in an incubator maintained at 37° C., 5% $CO_2$ for 4 days in order to induce the differentiation of CD4 positive T cells into Treg 17 cells.

Example 2

Analysis of the Effect of Poly-Gamma-Glutamic Acid on the Differentiation into Th17 Cells <2-1> Flow Cytometric Analysis on Intracellular Cytokines $10^6$ cells were collected from each of the differentiation induced cells prepared in Examples <1-2> and <1-3>, and restimulated for 6 hours by adding 40 ng/ml PMA (Sigma-Aldrich, USA), 1 μg/ml ionomycin (Sigma-Aldrich, USA) and 0.6 μl/ml Golgi-stop (BD Bioscience, USA). Then, the cells were washed and stained with anti-CD4-APC (eBioscience, USA). The thus stained cells were fixed and permeabilized with BD buffer solution (Cytofix/Cytoperm buffer) (BD Biosciences, USA).

The thus fixed cells were stained with anti-IL-17-PE antibody (eBioscience, USA) and anti-IFN-γ-FITC antibody (eBioscience, USA), and the ratio of fluorescence-stained cells was then measured by flow cytometric analysis.

First, when the cells were not treated with poly-gamma-glutamic acid, among the cells differentiated under the Th0 differentiation conditions, a higher percentage of cells showed IFN-γ expression over the IL-17 expression, whereas, among the cells differentiated under the Th17 differentiation conditions, a higher percentage of cells showed IL-17 expression over the IFN-γ expression (FIG. 1). From the above results, it was confirmed that, unlike under the Th0 differentiation conditions, the CD4 positive T cells are differentiated into Th17 cells which produce IL-17 under the Th17 differentiation conditions.

Among the cells differentiated under the Th0 differentiation conditions, a higher percentage of cells showed a decrease in IFN-γ expression as the concentration of poly-gamma-glutamic acid increased, but there was no significant change in the percentage of cells that expressed IL-17. In contrast, among the cells differentiated under the Th17 differentiation conditions, a higher percentage of cells showed a decrease in IL-17 expression as the concentration of poly-gamma-glutamic acid increased, but there was no significant change in the percentage of cells that expressed IFN-γ (FIG. 1). From the results as described above, it was confirmed that the poly-gamma-glutamic acid suppresses the differentiation of the CD4 positive T cells into the Th17 cells under the Th17 differentiation conditions, and also that this suppressive effect of the poly-gamma-glutamic acid is concentration-dependent.

In addition, $10^6$ cells were collected from each of the differentiation induced cells prepared in Examples <1-2> and <1-3> by treatment with 0 to 40 μM poly-gamma-glutamic acid, and restimulated for 6 hours by adding 40 ng/ml PMA, 1 μg/ml ionomycin and 0.6 μl/ml Golgi-stop. Then, the cells were washed and stained with anti-CD4-APC. The thus stained cells were fixed and permeabilized with BD buffer solution (Cytofix/Cytoperm buffer) (BD Biosciences, USA). The thus fixed cells were stained with anti-RORγt-PE antibody (eBioscience, USA) and anti-Foxp3-FITC antibody (eBioscience, USA), and the ratio of the fluorescence-stained cells was then measured by flow cytometric analysis.

Figure 2:
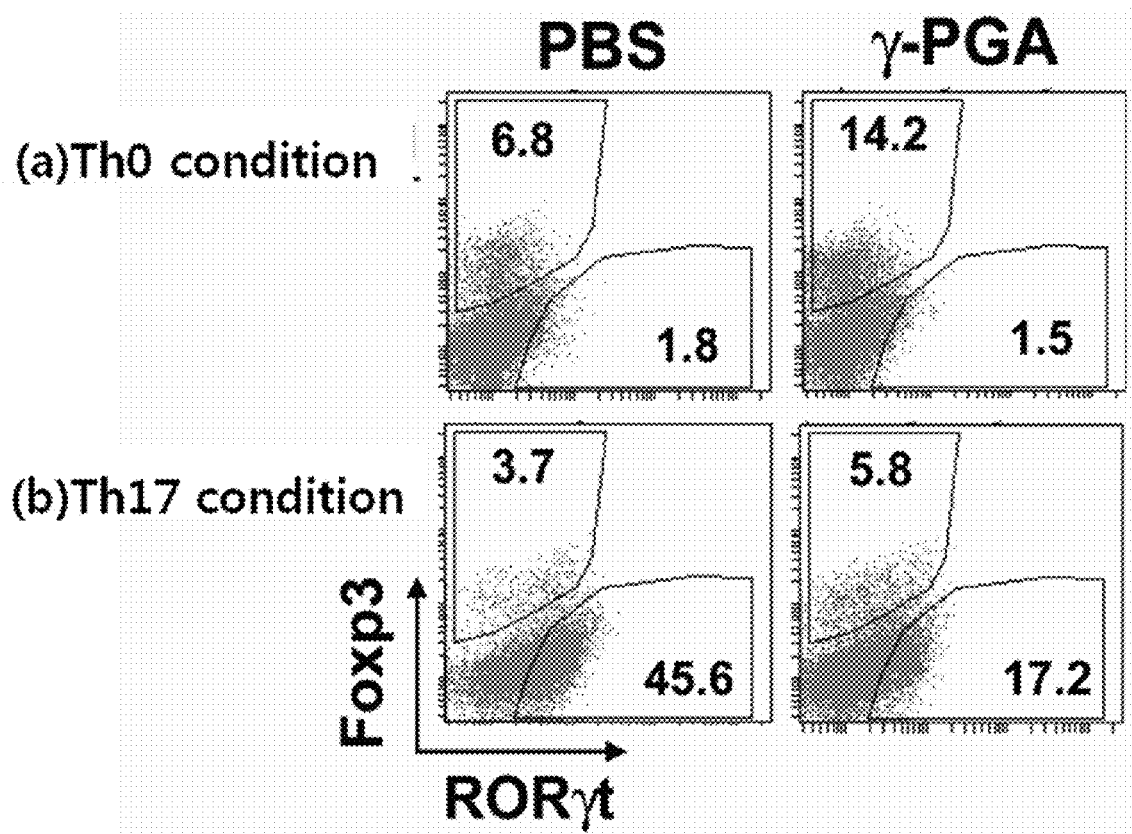
FIG. 2 is a graph illustrating the effect of poly-gamma-glutamic acid on the differentiation of naïve CD4+ T cells into Th17 cells and Treg cells under Th0 differentiation conditions (a) and Th17 differentiation conditions (b) via flow cytometric analysis using an anti-RORγt-PE antibody and an anti-Foxp3-FITC antibody.

First, when the cells were not treated with the poly-gamma-glutamic acid, among the cells differentiated under the Th0 differentiation conditions, a higher percentage of cells showed Foxp3 expression over the RORγt expression, whereas, among the cells differentiated under the Th17 differentiation conditions, a higher percentage of cells showed RORγt expression over the Foxp3 expression (FIG. 2).

Among the cells differentiated under the Th0 differentiation conditions, the percentage of cells that expressed Foxp3 when treated with the poly-gamma-glutamic acid increased about 2.5 times, but there was no significant change in the percentage of cells that expressed RORγt (FIG. 2($a$)). In contrast, among the cells differentiated under the Th17 differentiation conditions, the percentage of cells that expressed RORγt decreased to 0.4 times when treated with the poly-gamma-glutamic acid, but there was no significant change in the percentage of cells that expressed Foxp3 (FIG. 2($b$)). From the results as described above, it was confirmed that the poly-gamma-glutamic acid suppresses the differentiation of the CD4 positive T cells into the Th17 cells under the Th17 differentiation conditions.

<2-2> Cytokine ELISA

The culture medium of each of the differentiation induced cells prepared in Examples <1-2> and <1-3> by the treatment of 0 and 40 μM of poly-gamma-glutamic acid were centrifuged at 1,400 rpm for 7 minutes, and the resulting supernatant recovered therefrom was measured for its IL-17 concentration according to sandwich ELISA using R&D Duoset ELISA development system (R&D Systems, USA). In measuring the above IL-17 concentration, anti-IL-17-PE antibody (eBioscience, USA) was used.

Figure 3:
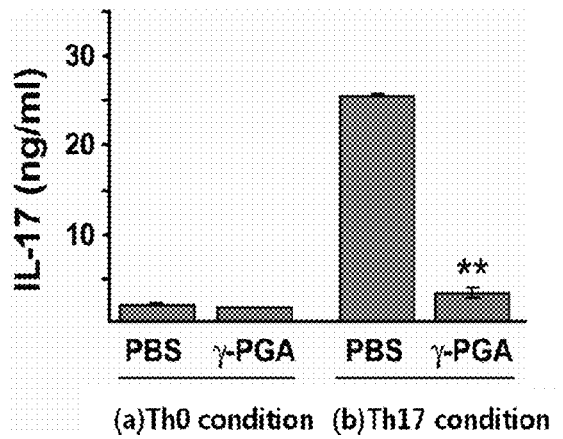
FIG. 3 is a graph illustrating the result of measurement of IL-17 cytokine production via enzyme-linked immunosorbent assay (ELISA) using anti-IL-17-PE antibody, after naïve CD4+ T cells are differentiated under Th0 differentiation conditions (a) and Th17 differentiation conditions (b) by either treating or untreating with poly-gamma-glutamic acid.

According to the result, the cells differentiated under the Th0 differentiation conditions basically showed a low IL-17 concentration, and there was no significant change in IL-17 concentration even in those treated with 40 μM poly-gamma-glutamic acid (FIG. 3($a$)). In contrast, the cells differentiated under the Th17 differentiation conditions basically showed about 25 ng/ml of IL-17, and those treated with 40 μM poly-gamma-glutamic acid showed a decrease to about one fifth in IL-17 concentration (FIG. 3($b$)). From the results as described above, it was confirmed that the poly-gamma-glutamic acid suppresses the differentiation of the CD4 positive T cells into the Th17 cells under the Th17 differentiation conditions.

<2-3> Analysis by Quantitative RT-PCR $8\times10^6$ cells were collected from the differentiation induced cells prepared in Examples <1-2> and <1-3> by the treatment of 0 and 40 μM of poly-gamma-glutamic acid, respectively, and then total RNA was obtained from the cells using TRI-ZOL agent (Invitrogen, USA), and cDNA was synthesized from the total RNA using reverse-transcriptase. Quantitative RT-PCR was performed using the synthesized cDNA and the primers listed in the following Table 1.

TABLE 1

List of Primers for the Analysis of Th17 cells

| Target Genes | SEQ ID NO. | forward primer (5' → 3')<br>reverse primer (5' → 3') |
|---|---|---|
| IL-17 | 1<br>2 | TCC AGA AGG CCC TCA GAC TA<br>AGC ATC TTC TCG ACC CTG AA |
| IL-17F | 3<br>4 | GTG TTC CCA ATG CCT CAC TT<br>CTC CTC CCA TGC ATT CTG AT |
| IL-21 | 5<br>6 | CGC CTC CTG ATT AGA CTT CG<br>TGT TTC TTT CCT CCC CTC CT |
| RORγt | 7<br>8 | CCG CTG AGA GGG CTT CAC<br>TGC AGG AGT AGG CCA CAT TA |
| STAT3 | 9<br>10 | ACC CAA CAG CCG CCG TAG<br>CAG ACT GGT TGT TTC CAT TCA GAT |
| IRF4 | 11<br>12 | CAC CAA AGC ACA GAG TCA CC<br>TCC TCT GGA TGG CTC CAG ATG |
| Ahr | 13<br>14 | AGC ATC ATG AGG AAC CTT GG<br>GGA TTT CGT CCG TTA TGT CG |

Figure 4:
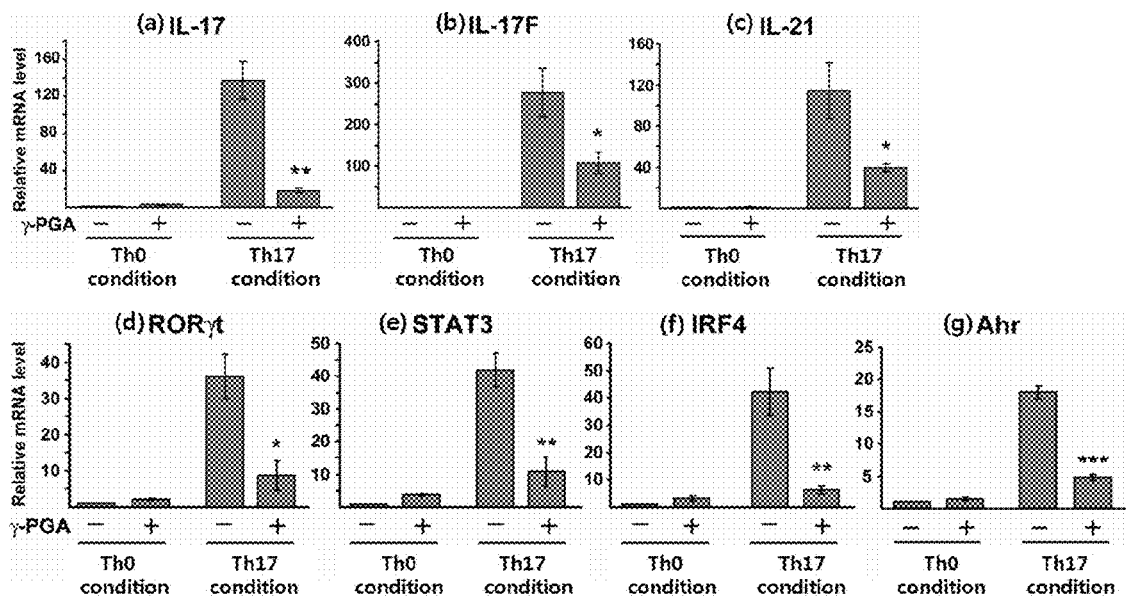
FIG. 4 shows graphs illustrating the result of measurement of the expression of various cytokines ((a): IL-17, (b): IL-17F, (c): IL-21) and transcription factors ((d): RORγt, (e): STAT3, (f): IRF4, (g): Ahr), which are produced or expressed in differentiated cells after naïve CD4+ T cells are differentiated under a Th0 differentiation conditions and a Th17 differentiation conditions by either treating or untreating with poly-gamma-glutamic acid, via quantitative RT-PCR.

The results showed that the expression of transcription factors such as RORγt, STAT3, IRF4, and Ahr, which play an important role in the differentiation into Th17 cells by the treatment of poly-gamma-glutamic acid, decreased (FIG. 4 (d)-(g)), and also the expression level of cytokines such as IL-17, IL17-F, and IL21 decreased. From the results as described above, it was confirmed that the poly-gamma-glutamic acid is effective in suppressing the differentiation of the CD4 positive T cells into the Th17 cells by decreasing the expression of transcription factors such as RORγt, STAT3, IRF4, and Ahr, which are essential in the differentiation of CD4 positive T cells into Th17 cells, thereby decreasing the production of cytokines produced in Th17 cells such as IL-17, IL-17F, and IL-21.

Example 3

Analysis of the Effect of Poly-Gamma-Glutamic Acid on the Differentiation into Treg Cells <3-1> Setup of Positive Control The CD4 positive T cells purified in Example <1-1> were aliquoted at a concentration of $2 \times 10^6$ cells into a plate including 1 μg/ml anti-CD3 antibody (145-2C11; eBioscience, USA) and 1 μg/ml anti-CD28 antibody (37.51; BD Biosciences, a). The plate was treated with TGF-β (R&D Systems, USA), which is well known as Treg differentiation-inducing substance, at a concentration of 5 ng/ml, 4 ng/ml IL-2 (Peprotech, U.S.A.) was added thereto (hereinafter, 'Th0 differentiation conditions'), and culturing was performed in an RPMI/10F medium at a concentration of 1 ml/well in an incubator maintained at 37° C., 5% $CO_2$ for 4 days, thereby obtaining a positive control to study the effect of the poly-gamma-glutamic acid on the differentiation into Th17 cells.

<3-2> Flow Cytometric Analysis on Intracellular Cytokines $10^6$ cells were collected from each of the differentiation induced cells prepared in Examples <1-3> and <3-1>, then washed and stained with anti-CD4-APC antibody (eBioscience, USA) and anti-CD25-PE antibody (eBioscience, USA). The thus stained cells were fixed and permeabilized with eBioscience Fixation/Permeabilization buffer (eBioscience, USA). The cells were then treated with anti-Foxp3-FITC antibody (eBioscience, USA) and the percentage of fluorescence-stained cells was examined using a flow cytometry analyzer.

Figure 5:
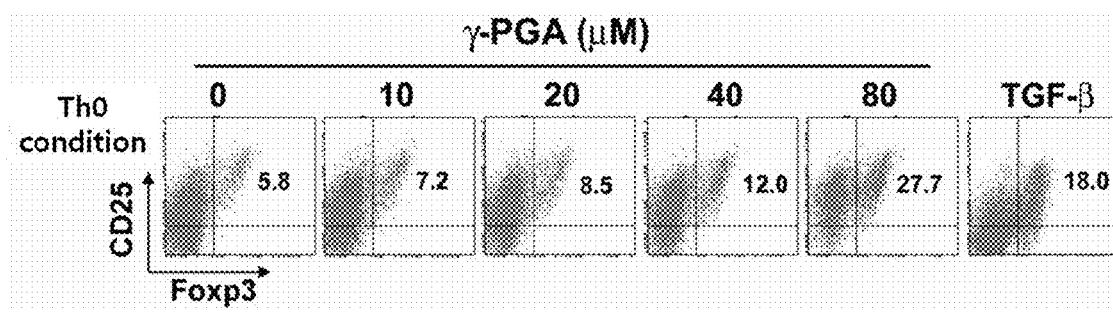
FIG. 5 is a graph illustrating the result of flow cytometric analysis, performed using an anti-Foxp3-FITC antibody, of naïve CD4+ T cells after the naïve CD4+ T cells are differentiated under a Th0 differentiation conditions by either treating or untreating with poly-gamma-glutamic acid or TGF-β.

The results showed that, among the cells differentiated under the Th0 differentiation conditions, the percentage of cells that expressed Foxp3 increased as the concentration of the poly-gamma-glutamic acid increased (FIG. 5). In particular, when the cells were treated with about 40 μM or higher concentration of poly-gamma-glutamic acid, the percentage of cells that expressed Foxp3 was similar to or higher than those when the differentiation of the cells were induced with 5 ng/ml TGF-β. From the results as described above, it was confirmed that the Th0 differentiation conditions promotes the differentiation into Treg cells which express Foxp3, and this effect of the poly-gamma-glutamic acid was concentration-dependent.

Further, among the cells differentiated under the Th17 differentiation conditions, the percentage of cells that expressed Foxp3 increased about 1.5 times by the treatment of 40 μM poly-gamma-glutamic acid (FIG. 2 (b)). From the results as described above, it was confirmed that the effect of the poly-gamma-glutamic acid to promote the differentiation into Treg cells is still maintained under the Th17 differentiation conditions.

<3-3> Analysis by Quantitative RT-PCR $8 \times 10^6$ cells were collected from the differentiation induced cells prepared in Example <1-3> by the treatment of 0 and 40 μM of poly-gamma-glutamic acid, then total RNA was obtained from the cells using TRIZOL reagent (Invitrogen, USA), and cDNA was synthesized from the total RNA using reverse-transcriptase. Quantitative RT-PCR was performed using the thus synthesized cDNA and the primers listed in the following Table 2.

TABLE 2

List of Primers for the Analysis of Treg cells

| Target Genes | SEQ ID NO. | forward primer (5' → 3')<br>reverse primer (5' → 3') |
|---|---|---|
| Foxp3 | 15<br>16 | CCT CAT GCA TCA GCT CTC CAC<br>AGA CTC CAT TTG CCA GCA GTG |

Figure 6:
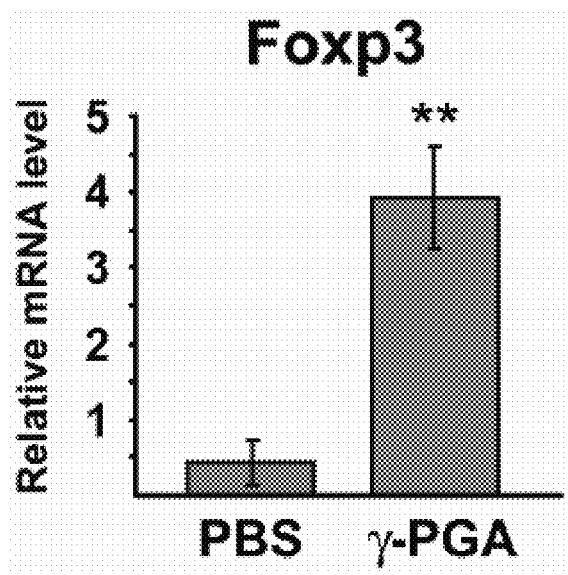
FIG. 6 is a graph illustrating the result of measurement of the expression of a Foxp3 gene, which is expressed in differentiated cells after naïve CD4+ T cells are differentiated under a Th0 differentiation conditions by either treating or untreating with poly-gamma-glutamic acid, via quantitative RT-PCR.

The results showed that the cells treated with 40 μM poly-gamma-glutamic acid showed about 8 times a higher level of Foxp3 expression compared to those untreated with poly-gamma-glutamic acid (FIG. 6). From the above-described results showing that the expression of the transcription factor, Foxp3, as a Treg cell-specific marker increased by the treatment of an increasing concentration of the poly-gamma-glutamic acid, it was confirmed that the poly-gamma-glutamic acid is effective in promoting the differentiation of the CD4 positive T cells into the Treg cells under the Th0 differentiation conditions.

<3-4> Flow Cytometric Analysis on Cell Surface Labelling $10^6$ cells were collected from each of the differentiation induced cells prepared in Example <1-3> by the treatment of 0 and 40 μM poly-gamma-glutamic acid, the differentiation induced positive control cells prepared in Example <1-3> by the treatment of TGF-β, and unsensitized splenocytes, and then washed and stained with anti-CD4-APC antibody (eBioscience, USA), anti-Foxp3-FITC antibody (eBioscience, USA), anti-CD25-PE antibody (eBioscience, USA), anti-GITR-PE antibody (eBioscience, USA) and anti-CTLA4-PE antibody (eBioscience, USA), and flow cytometric analysis was performed thereon. For the analysis of the phenotype of Treg cells, CD4 positive and Foxp3 positive cells were analyzed by gating. CD4 positive and Foxp3 positive cells in unsensitized splenocytes correspond to natural Treg (hereinafter, 'nTreg') cells naturally generated in the thymus, whereas CD4 positive and Foxp3 negative cells in unsensitized splenocytes correspond to conventional T cells.

Figure 7:
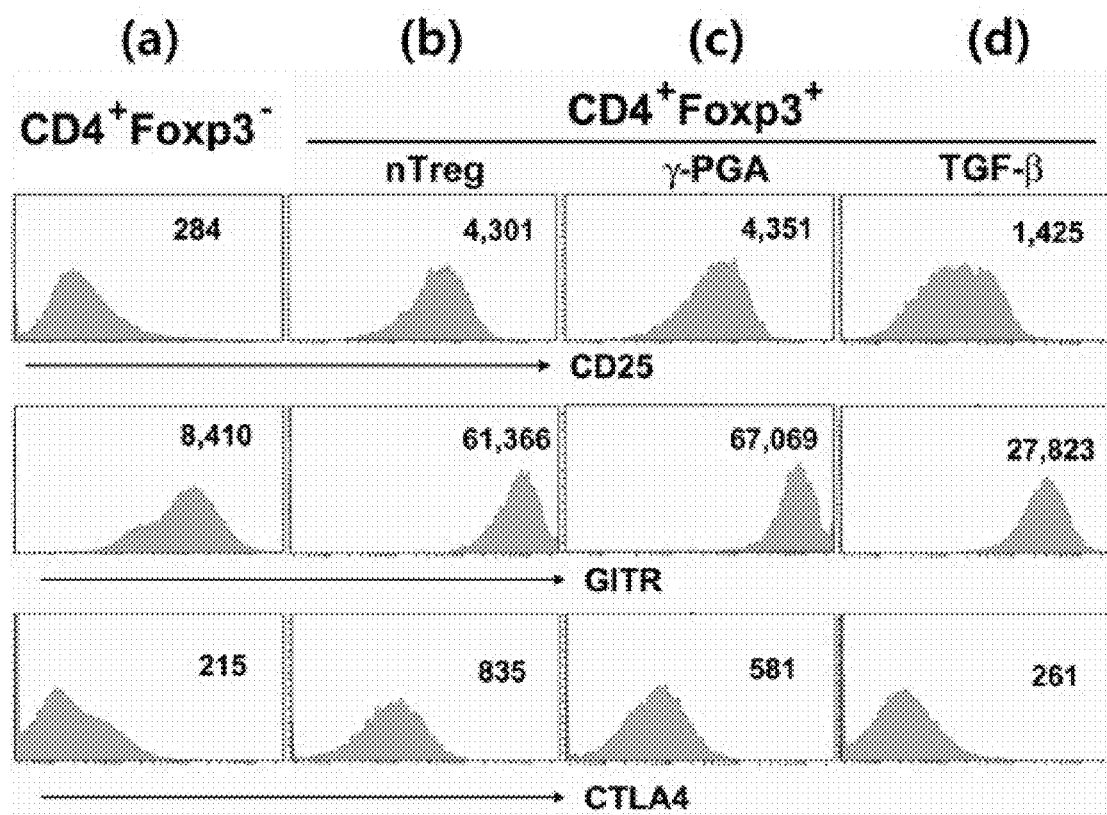
FIG. 7 shows graphs illustrating the result of flow cytometric analysis of conventional T cells (a), naturally occurring nTreg cells (b), Treg cells induced to differentiate by treating with poly-gamma-glutamic acid (c), and Treg cells induced to differentiate by treating with TGF-β (d) under a Th0 differentiation conditions using an anti-CD4-APC antibody, an anti-CD25-PE antibody, an anti-GITR-PE antibody and an anti-CTLA4-PE antibody.

The results showed that nTreg cells showed a higher expression of CD25, GITR, and CTLA4 genes as compared to that of conventional T cells (FIGS. 7(a) and (b)); with regard to the expression levels of the three genes, the Treg cells induced by the poly-gamma-glutamic acid showed an expression level similar to that of (1) the nTreg cells (FIG. 7(b)) but higher than that of the Treg cells induced by TGF-β (FIGS. 7 (c) and (d)). From the results as described above, it was confirmed that the Treg cells whose differentiation was induced had a similar phenotype to the nTreg cells naturally generated in the thymus Example 4

Figure 8:
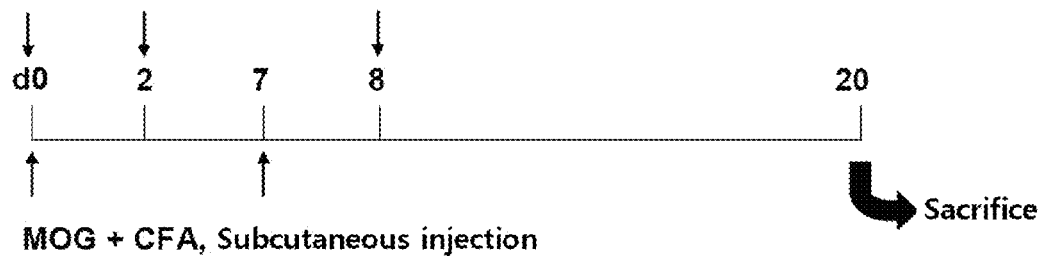
FIG. 8 is a schematic diagram illustrating the process of experimental autoimmune encephalomyelitis (EAE) induction in mice.

Therapeutic Effect of Poly-Gamma-Glutamic Acid on Th17-Mediated Diseases: Multiple Sclerosis <4-1> Preparation of Multiple Sclerosis Animal Model A multiple sclerosis animal model was prepared in order to study the therapeutic effect of poly-gamma-glutamic acid on Th17-mediated diseases. The above multiple sclerosis animal model was prepared according to the protocol described in Nurieva R et al. ((2007) Nature 448: 480-483) with a varying dose of pertussis toxin. More specifically, eighteen 8-10 week old female C57BL/6 mice were categorized into three different groups (6 mice/group): a normal control, a negative control (hereinafter, 'MOG group') and a test group (hereinafter, 'MOG/γPGA group'), and maintained under a specific-pathogen free (SPF) condition. Of the thus maintained three groups, the mice in the normal control were raised under the SPF condition by only being treated with PBS, and the mice in the MOG group and MOG/γPGA group were induced with experimental autoimmune encephalomyelitis (EAE) according to the scheme as shown in FIG. 8. In this case, the tests were designed as shown in Table 3 below.

TABLE 3

Experimental Design for Multiple Sclerosis Model Animal

| Group | Populations | EAE Induction | Drug Administered |
|---|---|---|---|
| normal control | 6 | x | PBS |
| MOG group | 6 | o | PBS |
| MOG/γPGA group | 6 | o | poly-gamma-glutamic acid (12 mg/day) |

The mice in the MOG group and MOG/γPGA group were all subcutaneously and intraperitoneally injected with a mixture including 150 μg of MOG35-55 (myelin oligodendrocyte glycoprotein peptides) (Peprotech, Korea) and 400 μg of CFA (complete Freund's Adjuvant) (Chondrex, USA) along with 500 ng of pertussis toxin (List Biological Laboratories, USA) on Day 0, respectively. Then, on Day 2, the 12 mice were intraperitoneally injected again with 500 ng of pertussis toxin, and on Day 7, subcutaneously injected again with MOG/CFA mixture. Finally, on Day 8, the mice were intraperitoneally injected with 200 ng of pertussis toxin to induce EAE in the mice in the MOG group and MOG/γPGA group.

During the EAE induction as described above, the mice in the MOG group were injected daily with PBS at a dose of 200 μl/day from Day 1, and the mice in MOG/γPGA group were intraperitoneally injected daily with poly-gamma-glutamic acid at a dose of 12 mg/day, which is dissolved in the 200 μl of PBS, from Day 1.

<4-2> Evaluation of the Effect of Poly-Gamma-Glutamic Acid on Clinical Symptoms

Evaluation of the effect of the poly-gamma-glutamic acid on clinical symptoms was performed on each group of mice categorized in Example <4-1>. The clinical symptoms were observed with the naked eye for each of the mice from Day 11 to Day 20 daily, each state of the mice was scored in terms of disease index, and each score was expressed by averaging the scores of the mice in each group. The disease index was evaluated from 0 points to 5 points based on the criteria shown in Table 4 below.

TABLE 4

Criteria for Measurement of Disease Index

| core | Clinical Symptoms |
|---|---|
| 5 | Death |
| 4 | Paralysis in front leg |
| 3 | Paralysis in hind leg |
| 2 | Paralysis in tail |
| 1 | Unstable walking |
| 0 | Normal |

The result revealed that the mice in the normal control in which EAE was not induced were all shown to be normal (disease index: 0); most mice in the MOG group showed paralysis on hind legs on Day 20 (disease index: 3) (FIG. 9). However, although EAE was induced in the mice in the MOG/γPGA group, the mice showed a disease index of about 0.7 on Day 20 indicating that their EAE symptoms were drastically improved (FIG. 9). From the results as described above, it was confirmed that the clinical symptoms of Th17-mediated diseases can be considerably alleviated by the administration of the poly-gamma-glutamic acid.

<4-3> Evaluation of the Histopathological Effect of Poly-Gamma-Glutamic Acid

The 18 mice categorized in Example <4-1> were all sacrificed on Day 20, and their spinal cord tissues were collected and fixed with 4% formalin solution. The thus fixed spinal cord tissues were embedded in paraffin, and cut into 6 μm thick specimens, which were then stained with hematoxylin-eosin. Thereafter, the damage level of spinal cord tissues and findings on the infiltration of inflammatory cells were observed under a microscope.

The results revealed that there was severe damage on spinal cord tissues and infiltration of white blood cells in the white matter in the MOG group (FIG. 10 (b)), whereas there was almost no damage on spinal cord tissues or infiltration of inflammatory cells observed in the normal control and the MOG/γPGA group (FIGS. 10(a) and (c)). From the results as described above, it was confirmed that the histopathological symptoms of Th17-mediated diseases can be significantly alleviated by the administration of the poly-gamma-glutamic acid.

<4-4> Observation of Inflammatory Cells in the Central Nervous System

The total 12 mice in the MOG group and MOG/γPGA group categorized in Example <4-1> were all sacrificed on Day 20, and their brains and spinal cord tissues were collected. Thus collected brain and spinal cord tissues were sliced into small pieces, dissolved using 500 mg/ml Liberase Blendzyme (Roche, Germany) and 100 mg/ml DNase I (Sigma-Aldrich, USA), and only mononuclear cells were obtained by Percoll concentration-gradient centrifugation. The thus obtained mononuclear cells were sensitized for 6 hours with 40 ng/ml PMA, 1 μg/ml ionomycin and 0.6 μl/ml Golgi-stop. Then, the cells were washed and stained with anti-CD4-APC (eBioscience, USA). The thus stained cells were fixed and permeabilized with eBioscience Fixation/Permeabilization buffer (eBioscience, USA). The thus fixed cells were stained with anti-IL-17-PE antibody (eBioscience, USA) and anti-IFN-γ-FITC antibody (eBioscience, USA), and then the percentage of fluorescence-stained cells was measured.

Figure 11:
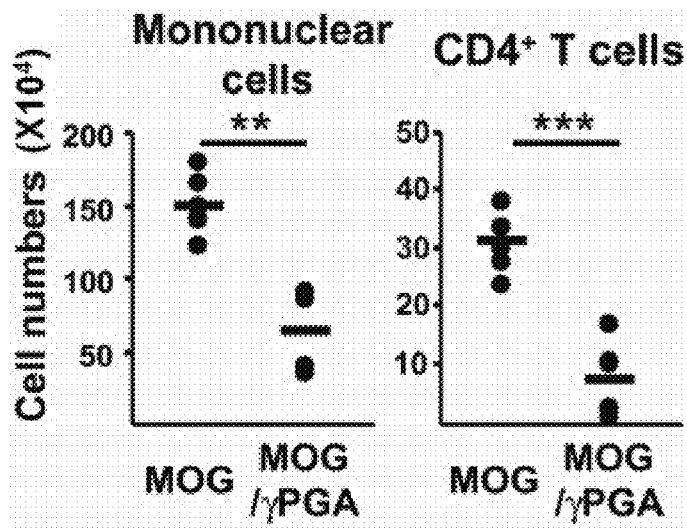
FIG. 11 is a graph illustrating the evaluation result of the suppressive effect of poly-gamma-glutamic acid on inflammatory response in an EAE mouse model.
Figure 12:
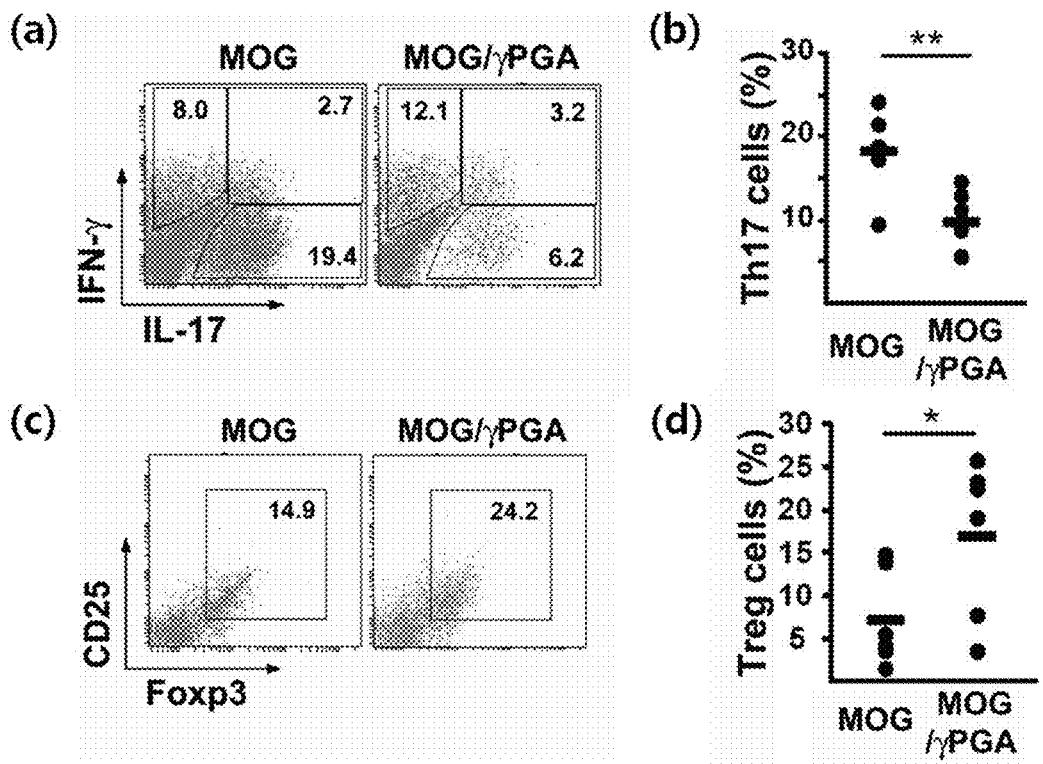
FIG. 12 shows graphs confirming the effect of poly-gamma-glutamic acid on suppression of differentiation into Th17 cells ((a) and (b)), and the effect of poly-gamma-glutamic acid on promotion of differentiation into Treg cells ((c) and (d)) in an EAE mouse model.

The results revealed that the number of mononuclear cells and CD4 positive T cells in the mice of the MOG/γPGA group was more significantly reduced than in that of the MOG group (FIG. 11). From the above-described results showing the decrease in mononuclear cells as inflammatory cells and CD4 positive T cells, it was confirmed that the treatment of the poly-gamma-glutamic acid can suppress inflammatory response.

Further, the percentage of Th17 cells, which produce IL-17, decreased to about half in the MOG/γPGA group as compared to that of the MOG group (FIGS. 12(a) and (b)). From the results as described above, it was confirmed that the poly-gamma-glutamic acid can suppress the differentiation into Th17 cells and reduce the production of IL-17 in vivo. Therefore, the poly-gamma-glutamic acid may be effectively used for the treatment of Th17-mediated diseases.

<4-5> Observation of Inflammatory Cells in the Immune System

The total 12 mice in the MOG group and MOG/γPGA group categorized in Example <4-1> were all sacrificed on Day 20, and their spleen tissues were collected. Thus collected spleen tissues were added into an RPMI/10F medium, pulverized to extract their cells, red blood cells and tissue residue were removed therefrom, and single cell suspension was finally obtained. The single cell suspension was washed and then stained with anti-CD4-APC antibody (eBioscience, USA) and anti-CD25-PE antibody (eBioscience, USA). The thus stained cells were fixed and permeabilized with eBioscience Fixation/Permeabilization buffer (eBioscience, USA), and then treatment with anti-Foxp3-FITC antibody (eBioscience, USA) was performed, and the percentage of the fluorescence-stained cells was examined via a flow cytometry analyzer.

The results revealed that the percentage of Treg cells which expressed Foxp3 and CD25 increased to about 1.5 times in the MOG/γPGA group as compared to that in the MOG group (FIGS. 12(c) and (d)). From the results as described above, it was confirmed that the poly-gamma-glutamic acid can suppress the differentiation into Treg cells in vivo. Therefore, the poly-gamma-glutamic acid may be effectively used for the treatment of Th17-mediated diseases.

Example 5

Therapeutic Effect of Poly-Gamma-Glutamic Acid on Th17-Mediated Diseases: Rheumatoid Arthritis <5-1> Preparation of Rheumatoid Arthritis Animal Model An animal model for rheumatoid arthritis which was a representative inflammatory disease and bone-destructive disease was prepared in order to study the therapeutic effect of poly-gamma-glutamic acid on Th17-mediated diseases, especially on Th17-mediated inflammatory diseases and Th17-mediated bone-destructive diseases. For the rheumatoid arthritis animal model, a collagen-induced arthritis (CIA) model was used. The CIA model requires a genetic background of DBA/1 mouse, and is induced much faster when the expression of IL-10 is reduced. In this Example, DBA/1 mice (hereinafter, 'IL-10KO DBA/1) with IL-10 gene knockout were used in order to increase the severity and progression rate of the disease more than that of normal CIA. More specifically, eight 6 to 8 week old male IL-10KO DBA/1 mice were categorized into two groups (a negative control (hereinafter, 'PBS group') and a test group (hereinafter, 'γPGA group'), allowed to adapt under a specific pathogen-free (SPF) condition for 7 days, and then the two groups of mice were all intradermally injected with a mixture including 100 μg type II collagen protein (Chodrex, USA) and an equal amount of CFA (Chondrex, USA) to induce CIA.

For a period of 3 weeks beginning on the 8$^{th}$ day after inducing CIA, the mice of the 'PBS group' were intraperitoneally administered with PBS three times a week at a dose of 200 μl per administration, whereas the mice of the 'γPGA group' were intraperitoneally administered with poly-gamma-glutamic acid and PBS three times a week at a dose of 12 mg/day and 200 μl per administration, respectively (FIG. 5).

TABLE 5

Experimental Animal Design for Rheumatoid Arthritis

| Group | Populations | CIA Induction | Drug Treated |
|---|---|---|---|
| PBS group | 4 | ○ | PBS |
| γPGA group | 4 | ○ | poly-gamma-glutamic acid (12 mg/treatment) |

<5-2> Evaluation of the Therapeutic Effect of Poly-Gamma-Glutamic Acid on Clinical Symptoms For the eight mice raised in Example <5-1>, the effect of the poly-gamma-glutamic acid on clinical symptoms for each group of mice was evaluated. The clinical symptoms were observed with the naked eye from the 7$^{th}$ day to the 34$^{th}$ day at intervals of 3 or 4 days, each state of the mice was scored as an arthritic index, and each score was expressed by averaging the scores of the mice in each group. Based on the criteria shown in Table 6 below, each leg was evaluated in the range of 0 point to 4 points, and the arthritic index for each subject was calculated by combining the scores of the four legs, and then expressed as an average value for each group. The incidence rate of each group refers to the percentage of legs with disease and is considered to have incidence when the score for each leg is 2 or higher.

TABLE 6

Measurement criteria for Arthritic Index

| Score | Clinical Symptoms |
|---|---|
| 4 | severe edema and erythema on ankle joint and entire foot, and twist in joint |
| 3 | moderate edema and erythema on ankle joint and talus |
| 2 | slight edema and erythema on ankle joint and talus |
| 1 | slight edema and erythema on foot and toes |
| 0 | normal |

The result revealed that the TBS group' showed the onset of incidence on Day 20 and about 70% of the group showed severe arthritis at their legs on Day 34 (arthritic index: about 9.5; incidence rate: about 70%) (FIGS. 13(a) and (b)). However, in the case of the 'γPGA group', unlike the TBS group', despite the induction of CIA, the onset of incidence was observed on Day 31, with slight arthritis on about 6% of legs on Day 34 (arthritic index: about 1; incidence rate: about 6%), indicating that the clinical symptoms of CIA were significantly alleviated (FIGS. 13(a) and (b)). From the results as described above, it was confirmed that the clinical symptoms of CIA, Th17-mediated diseases, can be considerably alleviated by the administration of the poly-gamma-glutamic acid.

<5-3> Histopathological Evaluation on the Therapeutic Effect of Poly-Gamma-Glutamic Acid 1: Suppression of Inflammation The eight mice raised in Example <5-1> were sacrificed on Day 34, all their hind leg tissues were collected and fixed with a 4% formalin solution, and then decalcified with 5.5% EDTA. The thus treated joint tissues were embedded in paraffin, and cut into 6 μm thick specimens, which were then stained with hematoxylin-eosin. Thereafter, the infiltration of inflammatory cells within the joint tissues and findings on the damage level of cartilage and bones were observed under a microscope. Based on the criteria shown in Table 7 below, each leg of the mice was scored from 0 points to 4 points, and the average value for each group was calculated and indicated as a histopathological index.

TABLE 7

Measurement criteria for Histopathological Index

Score  Clinical Symptoms 4  loss of normal structure in joint tissues
3  severe infiltration of inflammatory cells, and penetration into bones and cartilage
2  moderate infiltration of inflammatory cells, and slight penetration into bones and cartilage
1  slight infiltration of inflammatory cells, but no damage to bones and cartilage
0  normal The results revealed that there were many infiltrations of white blood cells in joint tissues and serious penetration of cartilage and bones in the 'PBS group' (FIGS. 14(a) and (c)), while in the case of the 'γPGA group', there was almost no damage to tissues or infiltrations of inflammatory cells (FIGS. 14(b) and (d)). From the results as described above, it was confirmed that the inflammatory symptoms of CIA, Th17-mediated diseases, can be considerably alleviated by the administration of the poly-gamma-glutamic acid.

<5-4> Histopathological Evaluation on the Therapeutic Effect of Poly-Gamma-Glutamic Acid 2: Alleviation of Cartilage Damage The joint cartilage regions of the sliced paraffin specimens prepared as in Example <5-2> were specially stained with Toluidine blue or Safranin O, and the findings of damage on cartilage were observed under a microscope. The cartilages stained with Toluidine blue took on a bluish purple color and the cartilages stained with Safranin O took on red color.

The results revealed that the cartilage damage was so severe with the end portion of a lubricating joint almost disappearing in the 'PBS group' (FIG. 15(a)), while in the case of the 'γPGA group,' cartilage layers were shown to be almost normal (FIG. 15(b)). From the results as described above, it was confirmed that the damage on cartilage in CIA, Th17-mediated diseases, can be considerably alleviated by the administration of the poly-gamma-glutamic acid.

<5-5> Histopathological Evaluation on the Therapeutic Effect of Poly-Gamma-Glutamic Acid 3: Suppression of Differentiation into Osteoclasts The eight mice raised in Example <5-1> were all sacrificed on Day 34, and tali and calcanei were collected, fixed with 4% formaldehyde for one day, and decalcified with 12% EDTA. The thus treated joint tissues were embedded in paraffin, and cut into 3 μm thick specimens. Then, Tartarate Resistant Acid Phosphatase (TRAP), a marker enzyme of osteoclasts, was stained with Acid Phosphatase, Leukocyte (TRAP) kit (Sigma-Aldrich, USA) according to the manufacturer's protocol, and the distribution of osteoclasts within the tissues of tali and calcanei was observed under a microscope.

The results revealed that there were many osteoclasts observed in bone tissues of mice not injected with poly-gamma-glutamic acid, whereas almost no osteoclasts were observed in bone tissues of mice injected with poly-gamma-glutamic acid (FIG. 16). From the results as described above, it was confirmed that the production of osteoclasts in CIA, Th17-mediated diseases, can be considerably decreased by the administration of the poly-gamma-glutamic acid.

<5-6> Suppressive Effect of Poly-Gamma-Glutamic Acid Against the Differentiation of Osteoclast Precursors <5-6-1> Confirmation of Effect of Normal Mouse-Derived Osteoclast Precursors In order to identify the reasons for the decrease in the production of osteoclasts in tali and calcanei of CIA mice treated with poly-gamma-glutamic acid in Example <5-5>, the effect of the poly-gamma-glutamic acid on the differentiation of osteoclast precursors into osteoclasts was confirmed more specifically through experiments as set forth hereinbelow.

7 to 8 week old male C57BL/6 mice (Orient Co., Ltd., Korea) were sacrificed in a specific pathogen-free barrier facility at Hanyang University, Korea, according to the regulations of Institutional Animal Care and Use Committee, and femurs and tibias were obtained. The thus obtained femurs and tibias were cut off at both epiphyseal ends, and 1 to 2 ml of α-minimum essential medium (α-MEM) (hereinafter, 'α-MEM/10F') including 10% fetal bovine serum (FBS), 100 unit/ml penicillin, and 100 μg/ml streptomycin was injected into bone marrow cavity at one end to obtain bone marrow. Single cells were obtained from the thus obtained bone marrow, red blood cells and tissue residue were removed therefrom, and a single cell suspension was finally obtained. The above single cell suspension was cultured for 24 hours after adding 20 ng/ml M-CSF (Peprotech, United Kingdom) thereto, non-adherent cells that could be differentiated into osteoclast precursors were obtained therefrom, the non-adherent cells were cultured for 24 hours after adding 20 ng/ml M-CSF, and osteoclast precursors were finally obtained. The thus obtained osteoclast precursors were aliquoted into a 96-well plate at a concentration of $2 \times 10^4$ cell/well, treated with 50 ng/ml M-CSF and 50 ng/ml RANKL (Peprotech, United Kingdom), and cultured for 4 days in α-MEM/10F medium containing (test group) or not containing (control) 20 μM poly-gamma-glutamic acid to differentiate the osteoclast precursors into osteoclasts.

Tartarate Resistant Acid Phosphatase (TRAP), a marker enzyme of osteoclasts, of the thus differentiated cells was stained with Acid Phosphatase, Leukocyte (TRAP) kit (Sigma-Aldrich, USA) according to the manufacturer's protocol, and the distribution of osteoclasts within the tissues (multinucleated TRAP positive cells) was observed under a microscope.

Further, in order to confirm the formation of an actin ring, which plays a crucial role in bone absorption by osteoclasts, the culture broth was removed from the thus differentiated cells, and then the cells were fixed with 4% formaldehyde for 20 minutes. Then, the cells were washed with distilled water, treated with 0.6 mM FITC-conjugated phalloidin for tagging the formed actin ring, and the actin ring formation was observed under a fluorescent microscope.

Figure 17:
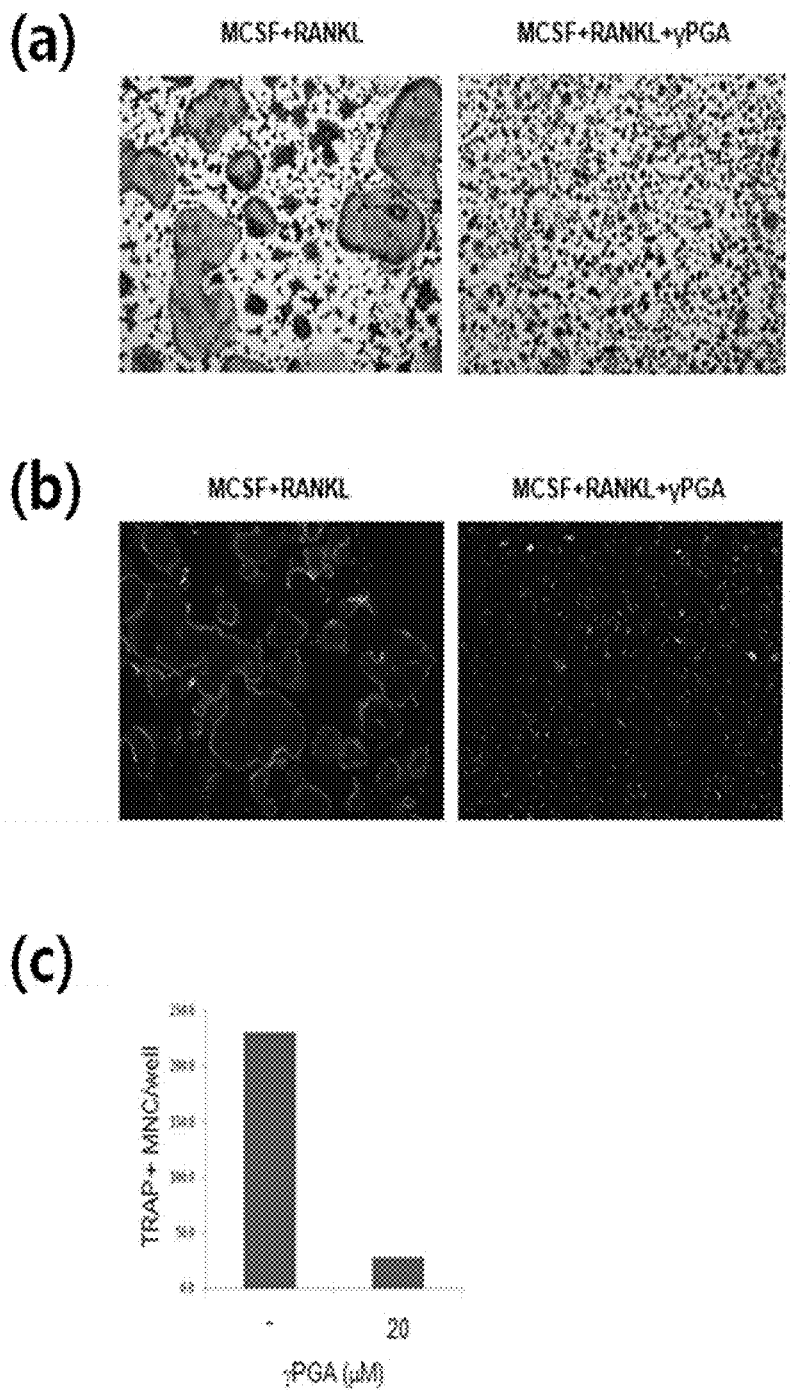
FIG. 17($a$) and FIG. 17($b$) are microscopic pictures depicting the result of a suppressive effect of poly-gamma-glutamic acid against the differentiation of normal mouse-derived osteoclast precursors into osteoclasts, thereby inhibiting actin ring formation, and FIG. 17($c$) is a graph depicting the number of osteoclasts after treating or untreating with poly-gamma-glutamic acid.

The result revealed that, in the control, in which cells were not treated with poly-gamma-glutamic acid, most osteoclast precursors differentiated into osteoclasts, whereas in a test group, in which cells were treated with the poly-gamma-glutamic acid, osteoclast precursors failed to differentiate into osteoclasts (FIGS. 17(a) and (c)). Further, the control showed an active formation of an actin ring while there was no actin ring formed in the test group, in which cells were treated with poly-gamma-glutamic acid (FIG. 17(b)). From the results as described above, it was confirmed that the poly-gamma-glutamic acid suppresses the differentiation of osteoclast precursors into osteoclasts.

<5-6-2> Confirmation of the Effect of Poly-Gamma-Glutamic Acid on Human Rheumatoid Arthritis Patient-Derived Osteoclast Precursors The applicability of the activity of poly-gamma-glutamic acid, which was confirmed in murine bone marrow cells in Example <5-6-1>, to human rheumatoid arthritis patient-derived cells was confirmed. To this end, the synovia was collected from the knee joints of patients diagnosed with rheumatoid arthritis at the Department of Rheumatology at Hanyang University Hospital for Rheumatic Diseases after giving detailed explanations to and obtaining approval from the patients. Mononuclear cells were obtained from the thus collected synovia via Ficoll density gradient centrifugation, and CD14 positive cells were selected as osteoclast precursors from the thus obtained mononuclear cells according to a Magnetic bead-Activated Cell Sorting (MACS) method. Then, the thus selected osteoclast precursors were aliquoted into a 96-well plate at a concentration of $6×10^4$ cells/well, treated with 20 ng/ml M-CSF and 40 ng/ml RANKL, and cultured for 9 days in an α-MEM/10F medium either containing poly-gamma-glutamic acid (test group) or not containing poly-gamma-glutamic acid (control) to differentiate the osteoclast precursors into osteoclasts.

In the thus differentiated cells, TRAP and an actin ring were stained in the same manner as in Example <5-6-1>, and the distribution of osteoclasts (multinucleated TRAP positive cells) and actin ring formation in the synovia were observed.

The result revealed that, in the control, in which cells were not treated with the poly-gamma-glutamic acid, most osteoclast precursors differentiated into osteoclasts, whereas in the test group, in which cells were treated with the poly-gamma-glutamic acid, osteoclast precursors failed to differentiate into osteoclasts (FIGS. 18(a) and (c)). Further, the control showed an active formation of an actin ring while there was no actin ring formed in the test group, in which cells were treated with the poly-gamma-glutamic acid (FIG. 18(b)). From the results as described above, it was confirmed that the poly-gamma-glutamic acid also suppresses the differentiation of osteoclast precursors derived from human rheumatoid arthritis patients into osteoclasts.

Next, the effect of poly-gamma-glutamic acid on the expression level of RANK and TREM2 genes, which are increased at the early stage of differentiation from osteoclast precursors to osteoclasts, was examined. The human rheumatoid arthritis patient-derived osteoclast precursors obtained thus were aliquoted into a 12-well culture dish at a concentration of $1.5×10^6$ cells/well, treated with 20 ng/ml M-CSF alone or along with 40 ng/ml RANKL. Then, the cells were cultured for 6 hours in an α-MEM/10F medium including 0 μM, 2 μM and 20 μM poly-gamma-glutamic acid, or cultured for 0, 6 or 24 hours in an α-MEM/10F medium including 20 μM poly-gamma-glutamic acid to differentiate the osteoclast precursors into osteoclasts.

Total RNA was obtained by treating the thus differentiated cells with TRIZOL agent (Invitrogen, USA), and cDNA was synthesized from the total RNA using reverse-transcriptase. Quantitative RT-PCR was performed using the thus synthesized cDNA and the primers listed in the following Table 8.

TABLE 8

List of Primers for Analysis of Osteoclasts

| Target Gene | SEQ ID NO. | forward primer (5' → 3') reverse primer (5' → 3') |
|---|---|---|
| RANK | 17 | CCA TCA TCT TTG GCG TTT G |
|  | 18 | AGC TGT GAG TGC TTT CCC T |
| TREM2 | 19 | AGC CTC TTG GAA GGA GAA AT |
|  | 20 | AGG AGG AGA AGG ATG GAA GT |

The result revealed that the test group which was treated with the poly-gamma-glutamic acid showed a significant decrease in the early expression of RANK and TREM2 genes, as compared to that of the control which was not treated with the poly-gamma-glutamic acid (FIGS. 19(a) and (b)), in particular, the expression of RANK and TREM2 genes gradually decreased as the time treated with the poly-gamma-glutamic acid increased (FIG. 19(b)). From the results as described above, it was confirmed that the poly-gamma-glutamic acid suppresses the expression of RANK and TREM2 genes.

From the results illustrated in FIGS. 18 and 19, it can be seen that the poly-gamma-glutamic acid suppresses the expression of RANK, a ligand of RANKL whose expression is increased by IL-17 secreted by Th17 cells, thereby inhibiting the differentiation of osteoclast precursors into osteoclasts. Further, the poly-gamma-glutamic acid is also shown to suppress the differentiation of human rheumatoid arthritis patient-derived osteoclast precursors into osteoclasts, and is thus effective in the treatment of Th17-mediated diseases.

The pharmaceutical composition of the present invention is effective in suppressing the differentiation into Th17 cells while promoting the differentiation into Treg cells. Accordingly, the pharmaceutical composition of the present invention can be useful in preventing and treating Th17-mediated diseases such as multiple sclerosis, rheumatoid arthritis, systemic lupus erythematosus, inflammatory bowel disease, Crohn's disease, and ankylosing spondylitis.

While the example embodiments of the present invention and their advantages have been described in detail, it should be understood that various changes, substitutions and alterations may be made herein without departing from the scope of the invention.

What is claimed is:

1. A method of reducing or inhibiting the differentiation of a naïve T cell into a Th17 cell, comprising:
    administering a daily dose of poly-gamma-glutamic acid to a subject with a Th17-mediated disease which is multiple sclerosis or rheumatoid arthritis, wherein the daily dose is in a range of 20 mg/ml to 60 mg/ml of poly-gamma-glutamic acid.

2. The method of claim 1, wherein the poly-gamma-glutamic acid has a molecular weight in the range of 1 kDa to 2000 kDa.

3. The method of claim 1, wherein the naïve T cell is a CD4 positive T cell.

4. The method of claim 1, wherein the Th17-mediated disease is induced by over-differentiation or over-growth of Th17 cells.

5. The method of claim 1, wherein the Th17-mediated disease is multiple sclerosis.

* * * * *

SEQUENCE LISTING

<160> NUMBER OF SEQ ID NOS: 20

<210> SEQ ID NO 1
<211> LENGTH: 20
<212> TYPE: DNA

<213> ORGANISM: Artificial Sequence
<220> FEATURE:
<223> OTHER INFORMATION: Forward Primer for IL-17

<400> SEQUENCE: 1
tccagaaggc cctcagacta                                          20

<210> SEQ ID NO 2
<211> LENGTH: 20
<212> TYPE: DNA
<213> ORGANISM: Artificial Sequence
<220> FEATURE:
<223> OTHER INFORMATION: Reverse Primer for IL-17

<400> SEQUENCE: 2
agcatcttct cgaccctgaa                                          20

<210> SEQ ID NO 3
<211> LENGTH: 20
<212> TYPE: DNA
<213> ORGANISM: Artificial Sequence
<220> FEATURE:
<223> OTHER INFORMATION: Forward Primer for IL-17F

<400> SEQUENCE: 3
gtgttcccaa tgcctcactt                                          20

<210> SEQ ID NO 4
<211> LENGTH: 20
<212> TYPE: DNA
<213> ORGANISM: Artificial Sequence
<220> FEATURE:
<223> OTHER INFORMATION: Reverse Primer for IL-17F

<400> SEQUENCE: 4
ctcctcccat gcattctgat                                          20

<210> SEQ ID NO 5
<211> LENGTH: 20
<212> TYPE: DNA
<213> ORGANISM: Artificial Sequence
<220> FEATURE:
<223> OTHER INFORMATION: Forward Primer for IL-21

<400> SEQUENCE: 5
cgcctcctga ttagacttcg                                          20

<210> SEQ ID NO 6
<211> LENGTH: 20
<212> TYPE: DNA
<213> ORGANISM: Artificial Sequence
<220> FEATURE:
<223> OTHER INFORMATION: Reverse Primer for IL-21

<400> SEQUENCE: 6
tgtttctttc ctcccctcct                                          20

<210> SEQ ID NO 7
<211> LENGTH: 18
<212> TYPE: DNA
<213> ORGANISM: Artificial Sequence
<220> FEATURE:
<223> OTHER INFORMATION: Forward Primer for ROR gamma t

<400> SEQUENCE: 7
ccgctgagag ggcttcac                                            18

<210> SEQ ID NO 8
<211> LENGTH: 20
<212> TYPE: DNA
<213> ORGANISM: Artificial Sequence
<220> FEATURE:
<223> OTHER INFORMATION: Reverse Primer for ROR gamma t

<400> SEQUENCE: 8
tgcaggagta ggccacatta                                              20

<210> SEQ ID NO 9
<211> LENGTH: 18
<212> TYPE: DNA
<213> ORGANISM: Artificial Sequence
<220> FEATURE:
<223> OTHER INFORMATION: Forward Primer for STAT3

<400> SEQUENCE: 9
acccaacagc cgccgtag                                                18

<210> SEQ ID NO 10
<211> LENGTH: 24
<212> TYPE: DNA
<213> ORGANISM: Artificial Sequence
<220> FEATURE:
<223> OTHER INFORMATION: Reverse Primer for STAT3

<400> SEQUENCE: 10
cagactggtt gtttccattc agat                                         24

<210> SEQ ID NO 11
<211> LENGTH: 20
<212> TYPE: DNA
<213> ORGANISM: Artificial Sequence
<220> FEATURE:
<223> OTHER INFORMATION: Forward Primer for IRF4

<400> SEQUENCE: 11
caccaaagca cagagtcacc                                              20

<210> SEQ ID NO 12
<211> LENGTH: 21
<212> TYPE: DNA
<213> ORGANISM: Artificial Sequence
<220> FEATURE:
<223> OTHER INFORMATION: Reverse Primer for IRF4

<400> SEQUENCE: 12
tcctctggat ggctccagat g                                            21

<210> SEQ ID NO 13
<211> LENGTH: 20
<212> TYPE: DNA
<213> ORGANISM: Artificial Sequence
<220> FEATURE:
<223> OTHER INFORMATION: Forward Primer for Ahr

<400> SEQUENCE: 13
agcatcatga ggaaccttgg                                              20

<210> SEQ ID NO 14
<211> LENGTH: 20
<212> TYPE: DNA
<213> ORGANISM: Artificial Sequence
<220> FEATURE:

```
<223> OTHER INFORMATION: Reverse Primer for Ahr

<400> SEQUENCE: 14
ggatttcgtc cgttatgtcg                                                    20

<210> SEQ ID NO 15
<211> LENGTH: 21
<212> TYPE: DNA
<213> ORGANISM: Artificial Sequence
<220> FEATURE:
<223> OTHER INFORMATION: Forward Primer for Foxp3

<400> SEQUENCE: 15
cctcatgcat cagctctcca c                                                  21

<210> SEQ ID NO 16
<211> LENGTH: 21
<212> TYPE: DNA
<213> ORGANISM: Artificial Sequence
<220> FEATURE:
<223> OTHER INFORMATION: Reverse Primer for Foxp3

<400> SEQUENCE: 16
agactccatt tgccagcagt g                                                  21

<210> SEQ ID NO 17
<211> LENGTH: 19
<212> TYPE: DNA
<213> ORGANISM: Artificial Sequence
<220> FEATURE:
<223> OTHER INFORMATION: Forward primer for RANK

<400> SEQUENCE: 17
ccatcatctt tggcgtttg                                                     19

<210> SEQ ID NO 18
<211> LENGTH: 19
<212> TYPE: DNA
<213> ORGANISM: Artificial Sequence
<220> FEATURE:
<223> OTHER INFORMATION: Reverse primer for RANK

<400> SEQUENCE: 18
agctgtgagt gctttccct                                                     19

<210> SEQ ID NO 19
<211> LENGTH: 20
<212> TYPE: DNA
<213> ORGANISM: Artificial Sequence
<220> FEATURE:
<223> OTHER INFORMATION: Forward primer for TREM2

<400> SEQUENCE: 19
agcctcttgg aaggagaaat                                                    20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for TREM2

<400> SEQUENCE: 20
aggaggagaa ggatggaagt                                                    20
```